United States Patent [19]

Takaya et al.

[11] Patent Number: 5,594,132

[45] Date of Patent: Jan. 14, 1997

[54] 7-ACYLAMINO-3-SUBSTITUTED CEPHALOSPORANIC ACID DERIVATIVES

[75] Inventors: Takao Takaya, Kawanishi; Hisashi Takasugi, Kohama-nishi; Takashi Masugi, Ikeda; Hideaki Yamanaka, Hirakata; Kohji Kawabata, Sumiyoshi, all of Japan

[73] Assignee: Fujisawa Pharmaceutical Co., Ltd., Osaka, Japan

[21] Appl. No.: 684,194

[22] Filed: Apr. 12, 1991

Related U.S. Application Data

[62] Division of Ser. No. 461,340, Jan. 5, 1990, Pat. No. 5,026,695, which is a division of Ser. No. 785,048, Oct. 9, 1985, Pat. No. 4,904,652, which is a continuation of Ser. No. 489,236, Apr. 28, 1983, abandoned, which is a division of Ser. No. 206,831, Nov. 14, 1980, Pat. No. 4,409,215.

[30] Foreign Application Priority Data

| Nov. 19, 1979 | [GB] | United Kingdom | 7939985 |
|---|---|---|---|
| Feb. 8, 1980 | [GB] | United Kingdom | 8004335 |
| Apr. 21, 1980 | [GB] | United Kingdom | 8012991 |

[51] Int. Cl.[6] .................. C07D 501/36; C07D 501/34
[52] U.S. Cl. .................. 540/227; 540/230; 540/229; 540/228; 540/226
[58] Field of Search .................. 540/227, 230, 540/229, 228, 226

[56] References Cited

U.S. PATENT DOCUMENTS

| 3,647,788 | 3/1972 | Clark et al. | 260/243 C |
|---|---|---|---|
| 3,665,003 | 5/1972 | Kennedy et al. | 424/246 |
| 3,960,849 | 6/1976 | Breuer | 424/246 |
| 4,024,249 | 5/1977 | Müller et al. | 424/246 |
| 4,033,950 | 7/1977 | Cook et al. | 544/22 |
| 4,067,976 | 1/1978 | Hoover et al. | 424/246 |
| 4,080,498 | 3/1978 | Numata et al. | 544/27 |
| 4,098,888 | 7/1978 | Ochiai et al. | 544/27 |
| 4,166,115 | 8/1979 | Takaya et al. | 424/246 |
| 4,278,793 | 7/1981 | Durckheiner et al. | 544/27 |
| 4,294,960 | 10/1981 | Takaya | 540/222 |
| 4,338,436 | 7/1982 | Herron | 540/222 |
| 4,409,215 | 11/1983 | Takaya et al. | 544/27 |
| 4,425,341 | 1/1984 | Takaya et al. | 544/16 |
| 4,462,999 | 7/1984 | Takaya et al. | 544/27 |
| 4,912,212 | 3/1990 | Ochiai et al. | 540/222 |

FOREIGN PATENT DOCUMENTS

| 0034536 | 8/1981 | European Pat. Off. |
|---|---|---|
| 2422385 | 11/1974 | Germany . |
| 1261780 | 1/1972 | United Kingdom . |
| 1332448 | 10/1973 | United Kingdom . |
| 1389194 | 4/1975 | United Kingdom . |

OTHER PUBLICATIONS

Wolff, Manfred, *Burger's Medicinal Chemistry*, Wiley–Interscience, New York (1979) pp. 130, 131 and 138.

Burger, Alfred, *Medicinal Chemistry*, 3rd. Ed., (1970) pp. 52–53.

*Primary Examiner*—John M. Ford
*Attorney, Agent, or Firm*—Oblon, Spivak, McClelland, Maier & Neustadt, P.C.

[57] ABSTRACT

A compound of the formula:

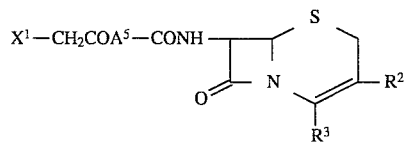

in which $R^2$ is lower alkoxymethyl, lower alkylthiomethyl or lower alkenylthiomethyl, $R^3$ is carboxy or a protected carboxy group, $A^5$ is lower alkylene which may have a group of the formula: $=N-OR^6$, wherein $R^6$ is hydrogen, lower alkenyl, lower alkynyl, lower alkyl or lower alkyl substituted by one or more substituent (s) selected from carboxy, a protected carboxy group, amino, a protected amino group and a heterocyclic group, and $X^1$ is halogen, or a salt thereof.

5 Claims, No Drawings

7-ACYLAMINO-3-SUBSTITUTED CEPHALOSPORANIC ACID DERIVATIVES

This is a division, of application Ser. No. 07/461,340, filed on Jan. 5,1990, now U.S. Pat. No. 5,026,695, which is a division of Ser. No. 06/785,048, filed on Oct. 9, 1985, now U.S. Pat. No. 4,904,652, which is a Continuation of application Ser. No. 06/489,236, filed Apr. 28, 1983, abandoned, which is a Divisional of application Ser. No. 06/206,831, filed Nov. 14, 1980, now U.S. Pat. No. 4,409,215.

The present invention relates to novel 7-acylamino-3-substituted cephalosporanic acid derivatives and pharmaceutically acceptable salts thereof.

More particularly, it relates to novel 7-acylamino-3-substituted cephalosporanic acid derivatives and pharmaceutically acceptable salts thereof, which have antimicrobial activity, to processes for the preparation thereof, to a pharmaceutical composition comprising the same, and to a method of using the same therapeutically in the treatment of infectious diseases in human being and animals.

Accordingly, one object of the present invention is to provide novel 7-acylamino-3-substituted cephalosporanic acid derivatives and pharmaceutically acceptable salts thereof, which are highly active against a number of pathogenic microorganisms and are useful as antimicrobial agents, especially oral administration.

Another object of the present invention is to provide processes for the preparation of novel 7-acylamino-3-substituted cephalosporanic acid derivatives and salts thereof.

A further object of the present invention is to provide a pharmaceutical composition comprising, as active ingredients, said 7-acylamino-3-substituted cephalosporanic acid derivatives and pharmaceutically acceptable salts thereof.

Still further object of the present invention is to provide a method of using said 7-acylamino-3-substituted cephalosporanic acid derivatives and pharmaceutically acceptable salts thereof in the treatment of infectious diseases by pathogenic microorganisms in human being and animals.

The object 7-acylamino-3-substituted cephalosporanic acid derivatives are novel and can be represented by the following general formula:

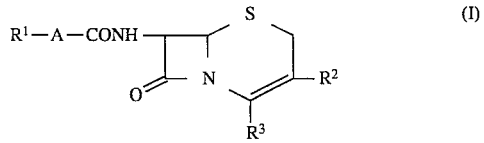

in which $R^1$ is a group of the formula:

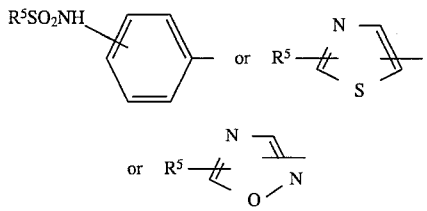

wherein $R^4$ is lower alkyl and $R^5$ is amino or a protected amino group, $R^2$ is lower alkoxymethyl, lower alkylthiomethyl or lower alkenylthiomethyl, $R^3$ is carboxy or a protected carboxy group, and A is lower alkylene which may have a substituent selected from the groups consisting of amino, a protected amino group, hydroxy, oxo and a group of the formula: $=N\text{--}OR^6$, wherein $R^6$ is hydrogen, lower alkenyl, lower alkynyl, lower alkyl or lower alkyl substituted by one or more substituent (s) selected from carboxy, a protected carboxy group, amino, a protected amino group, and heterocyclic group.

In the object compounds (I) and the corresponding starting compounds (II) to (IV) in Processes 1 and 7 mentioned below, it is to be understood that there may be one or more stereoisomeric pair (s) such as optical and geometrical isomers due to asymmetric carbon atom and double bond in those molecules and such isomers are also included within the scope of the present invention.

With regard to geometrical isomers in the object compounds and the starting compounds, it is to be noted that, for example, the object compounds, wherein A means a group of the formula: $=C=N\text{--}OR^6$, include syn isomer, anti isomer and a mixture thereof, and the syn isomer means one geometrical isomer having the partial structure represented by the following formula:

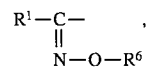

wherein $R^1$ and $R^6$ are each as defined above, and the anti isomer means the other geometrical isomer having the partial structure represented by the following formula:

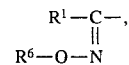

wherein $R^1$ and $R^6$ are each as defined above.

Regarding the other object and starting compounds as mentioned above, the syn isomer and the anti isomer can also be referred to the same geometrical isomers as illustrated for the compounds (I).

Suitable pharmaceutically acceptable salts of the object compounds (I) are conventional non-toxic salts and may include a salt with a base for an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); an intermolecular or intramolecular quaternary salt, and the like. The said intermolecular quaternary salt can be formed in case that the heterocyclic group in $R^6$ in the compounds (I) contains nitrogen atom (s) (e.g. pyridyl, etc.), and suitable intermolecular quaternary salt may include 1-lower alkylpyridinium lower alkylsulfate (e.g. 1-methylpyridinium methylsulfate, 1-ethylpyridinium ethylsulfate, etc.), 1-lower alkylpyridinium halide (e.g. 1-methylpyridinium iodide, etc.) and the like. The said intramolecular salt can be formed in case that heterocyclic group in $R^6$ in the compounds (I) contains nitrogen atom (s) (e.g. pyridyl etc.) and $R^3$ is carboxy, and suitable intramolecular salt may include 1-lower alkylpyridinium carboxylate (e.g. 1-methylpyridinium carboxylate, 1-ethylpyridinium carboxylate, 1-propylpyridinium carboxylate, 1-isopropylpyridinium carboxylate, 1-butylpyridinium carboxylate, etc.); and the like.

According to the present invention, the object compounds (I) and the pharmaceutically acceptable salts thereof can be prepared by the processes as illustrated by the following reaction schemes.

(1) Process 1:

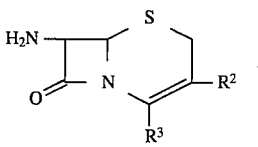

(II)
or its reactive
derivative at
the amino group
or a salt thereof $R^1-A-COOH$
(III)
or its reactive
derivative at the
carboxy group or
a salt thereof
$\longrightarrow$

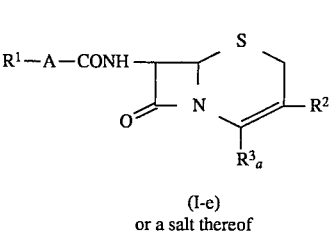

(I)
or a salt thereof (2) Process 2:

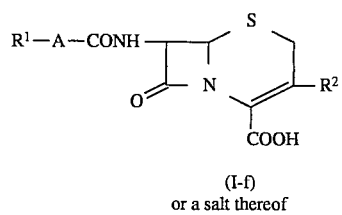

(I-a)
or a salt thereof

Removal of
the amino
protective
group in $A^1$
$\longrightarrow$

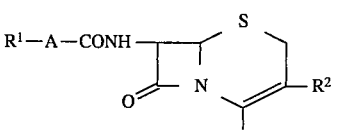

(I-b)
or a salt thereof (3) Process 3:

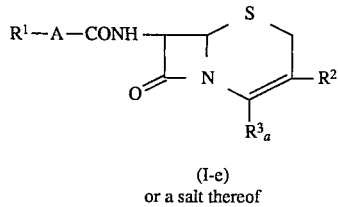

(I-c)
or a salt thereof

Removal of
the amino-
protective
group for $R^1_a$
$\longrightarrow$

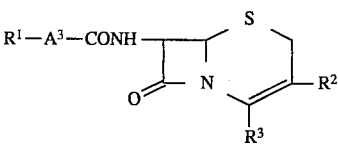

(I-d)
or a salt thereof (4) Process 4:

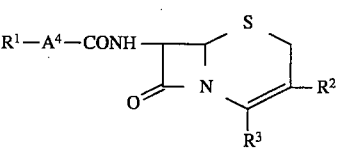

(I-e)
or a salt thereof

Removal of
the carboxy-
protective
group in $R^3_a$
$\longrightarrow$

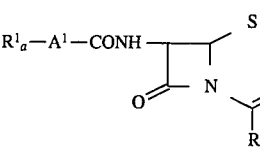

(I-f)
or a salt thereof (5) Process 5:

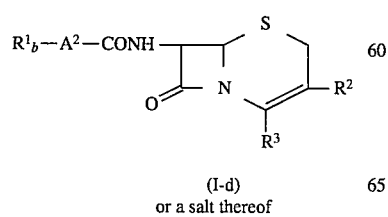

(I-f)
or a salt thereof

Introduction of
the carboxy-
protective group
$\longrightarrow$ (I-e)
or a salt thereof (6) Process 6:

(I-g)
or a salt thereof

Reduction $\longrightarrow$ (I-h)
or a salt thereof (7) Process 7:
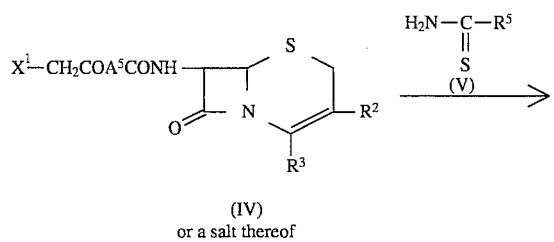
(IV)
or a salt thereof
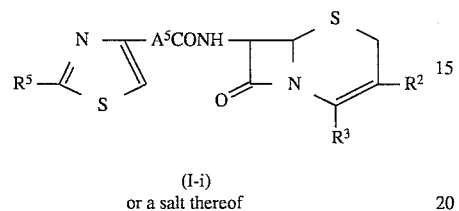
(I-i)
or a salt thereof
(8) Process 8:
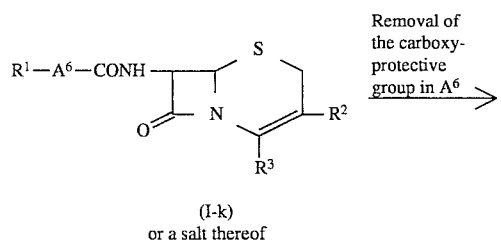
(I-k)
or a salt thereof
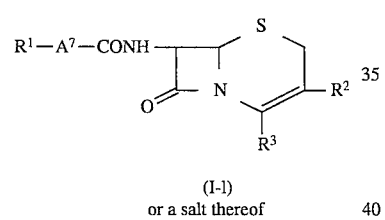
(I-l)
or a salt thereof
(9) Process 9:
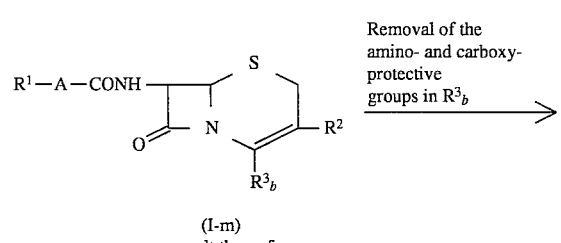
(I-m)
or a salt thereof
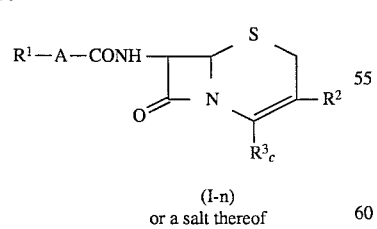
(I-n)
or a salt thereof
(10) Process 10:
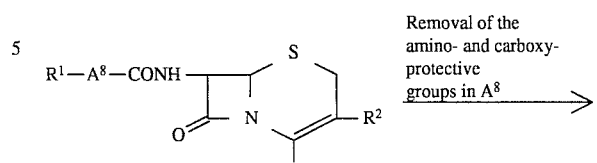
(I-o)
or a salt thereof
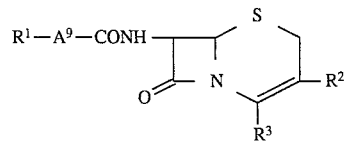
(I-p)
or a salt thereof
(11) Process 11:
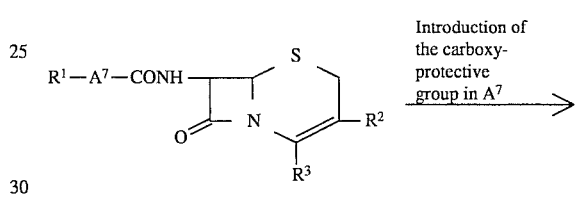
(I-l)
or a salt thereof
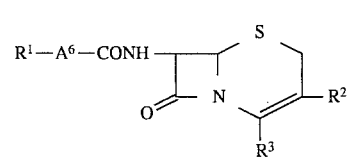
(I-k)
or a salt thereof
(12) Process 12:
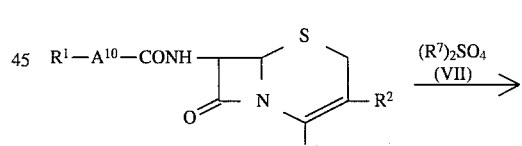
(I-q)
or a salt thereof
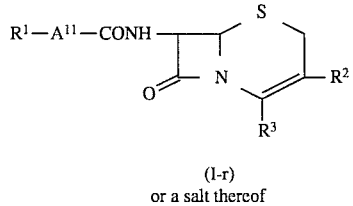
(I-r)
or a salt thereof

(13) Process 13:

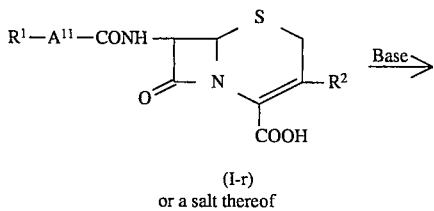

(I-r)
or a salt thereof

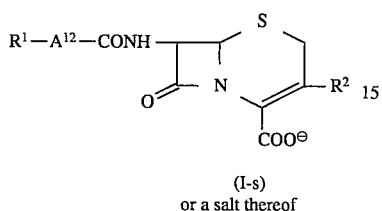

(I-s)
or a salt thereof in which
R¹, R², R³, R⁵ and A are each as defined above,
$R_a^1$ is a group of the formula:

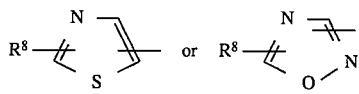

wherein R⁸ is a protected amino group,
$R_b^1$ is a group of the formula:

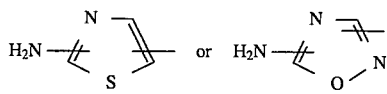

$R_a^3$ is a protected carboxy group,
$R_b^3$ is lower alkoxycarbonyl substituted by protected amino and protected carboxy groups,
$R_c^3$ is lower alkoxycarbonyl substituted by amino and carboxy,
R⁷ is lower alkyl,
A¹ is lower alkylene having a protected amino group,
A² is lower alkylene having an amino group,
A³ is lower alkylene having an oxo group,
A⁴ is lower alkylene having a hydroxy group,
A⁵ is lower alkylene which may have a group of the formula =N~OR⁶, wherein
R⁶ is as defined above,
A⁶ is lower alkylene having a group of the formula: =N~$OR_a^6$, wherein $R_a^6$ is lower alkyl substituted by a protected carboxy group,
A⁷ is lower alkylene having a group of the formula: =N~$OR_b^6$, wherein $R_b^6$ is lower alkyl substituted by carboxy,
A⁸ is lower alkylene having a group of the formula: =N~$OR_c^6$, wherein $R_c^6$ is lower alkoxycarbonyl(lower)alkyl substituted by protected amino and protected carboxy groups or lower alkyl substituted by protected amino and protected carboxy groups, A⁹ is lower alkylene having a group of the formula: =N~$OR_d^6$, wherein $R_d^6$ is lower alkoxycarbonyl(lower)alkyl substituted by amino and carboxy or lower alkyl substituted by amino and carboxy,
A¹⁰ is lower alkylene having a group of the formula: =N~$OR_e^6$, wherein $R_e^6$ is lower alkyl substituted by a group of the formula:

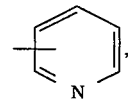

A¹¹ is lower alkylene having a group of the formula: =N~$OR_f^6$, wherein $R_f^6$ is lower alkyl substituted by a group of the formula:

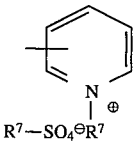

wherein R⁷ is as defined above,
A¹² is lower alkylene having a group of the formula: =N~$OR_g^6$, wherein $R_g^6$ is lower alkyl substituted by a cation of the formula:

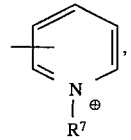

wherein R⁷ is as defined above, and
X¹ is halogen.
Some of the starting compounds (II), (III) and (IV) used in Processes 1 and 7 are new and can be represented by the following formula:

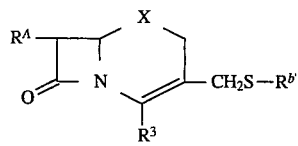

in which
$R^A$ is amino or a protected amino group,
$R^{b'}$ is lower alkenyl,
X is —S— or —SO—, and
R³ is as defined above,
and a salt thereof.

Suitable salts of the above starting compound are the same as those exemplified for the object compounds (I).

The starting compound thus formulated and other starting compounds can be prepared, for example, from the known compounds by the methods in the following reaction schemes, and others can be prepared in a similar manner thereto or in a conventional manner.

(A) Process A:
Preparation of some of the starting compounds (II)
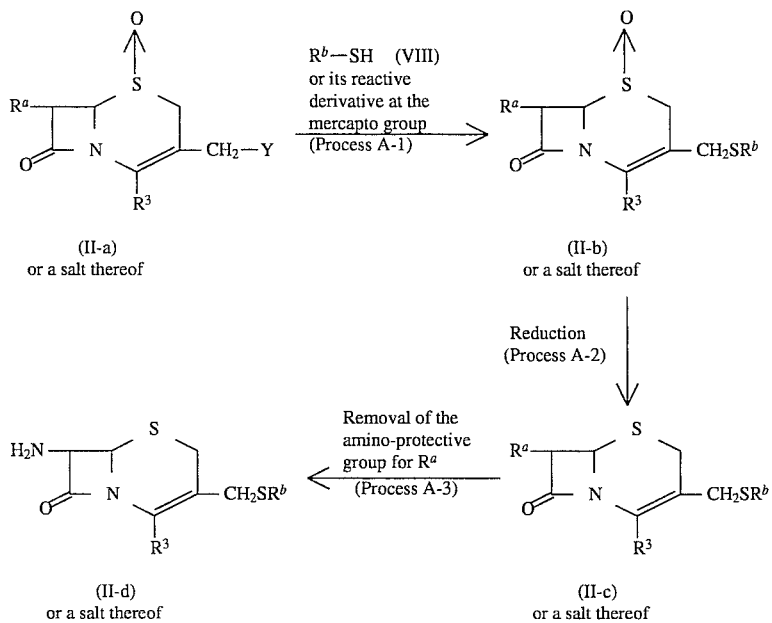
(II-a) or a salt thereof
(II-b) or a salt thereof
(II-d) or a salt thereof
(II-c) or a salt thereof
(B) Process B:
Preparation of some of the starting compounds (III)
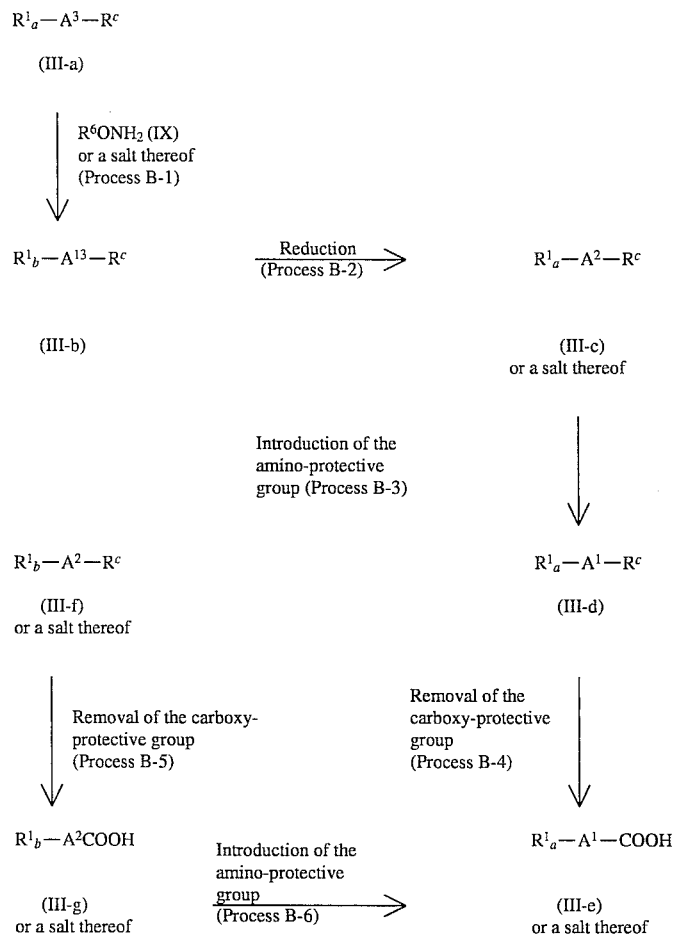
(III-a)
(III-b)
(III-c) or a salt thereof
(III-f) or a salt thereof
(III-d)
(III-g) or a salt thereof
(III-e) or a salt thereof
(C) Process C:

Preparation of some of the starting compounds (IV)

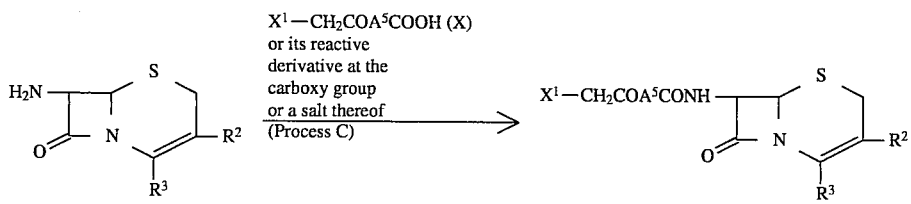

(IV-a)
or its reactive derivative
at the amino group or a
salt thereof (IV)
or a salt thereof (D) Process D:
Preparation of some of the compounds (II)

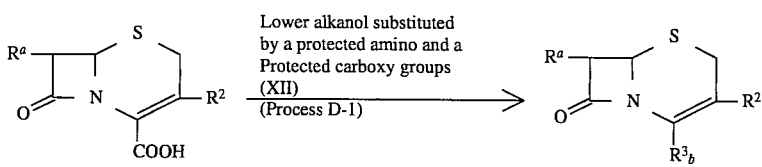

(II-e)
or a reactive derivative
at the carboxy group or
a salt thereof (II-f)
or a salt thereof Removal of the amino-
protective group for
$R^a$
(Process D-2)

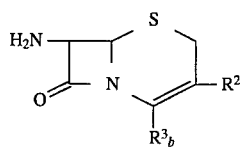

(II-g)
or a salt thereof (E) Process E:
Preparation of some of the compound (III) in Process 1

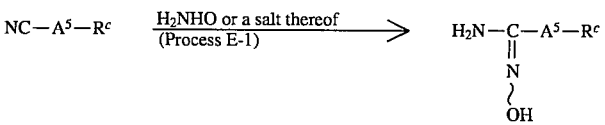

(III-h)

(III-i)

$R^2$—COOH (XIII)
or a reactive derivative
at the carboxy group or
a salt thereof
(Process E-2)

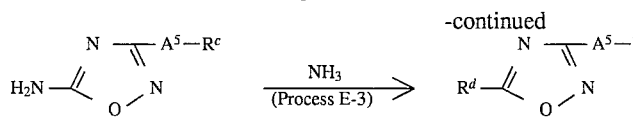

(III-k)
or a salt thereof (III-j)

Removal of the carboxy-
protective group for $R^c$
(Process E-4)

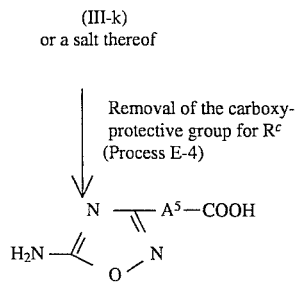

(III-l)
or a salt thereof (F) Process F:
Preparation of some of the reagent used in Process B-1

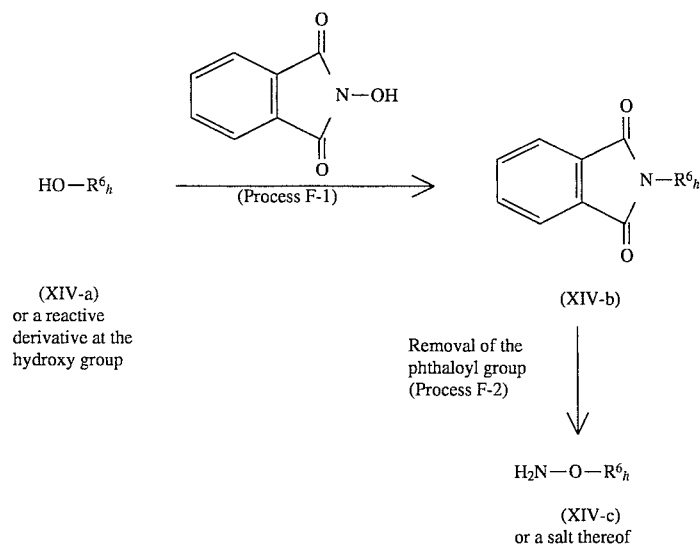

(XIV-a)
or a reactive
derivative at the
hydroxy group (XIV-b)

Removal of the
phthaloyl group
(Process F-2)

$H_2N-O-R^6_h$ (XIV-c)
or a salt thereof in which $R_a^1, R_b^1, R^2, R^3, R_b^3, R^6, A^1, A^2, A^3, A^5$ and $X^1$ are each as defined above, $R^a$ is a protected amino group, $R^b$ is lower alkyl or lower alkenyl, $R^c$ is a protected carboxy group or carboxy, $R^d$ is trihalomethyl, Y is a conventional group which is capable to be replaced by the residue ($-SR^b$) of the compound of the formula: $HS-R^b$, in which $R^b$ is as defined above, $A^{13}$ is lower alkylene having a group of the formula: $=N-OR^6$, wherein $R^6$ is as defined above, and $R_h^6$ is lower alkyl substituted by a protected carboxy group, lower alkoxycarbonyl (lower)alkyl substituted by protected amino and protected carboxy groups or lower alkyl substitued by protected amino and protected carboxy groups.

In the above and subsequent description of the present specification, suitable examples and illustration of the various definitions to be included within the scope thereof are explained in detail as follows.

The term "lower" in the present specification is intended to mean a group having 1 to 6 carbon atoms, unless otherwise indicated.

Suitable "lower alkyl" group may include straight or branched one such as methyl, ethyl, propyl, isopropyl, butyl, isobutyl, pentyl, isopentyl, neopentyl, hexyl and the like, in which the preferred one is $C_1-C_3$alkyl.

Suitable "lower alkenyl" group may include straight or branched one such as vinyl, 1-propenyl, allyl, 1-(or 2- or 3-)butenyl, 1-(or 2- or 3- or 4-)pentenyl, 1-(or 2- or 3- or 4- or 5-)hexenyl, 2-methyl -2-propenyl, and the like, in which the preferred one is $C_2-C_5$alkenyl.

Suitable "lower alkynyl" group may include straight or branched one such as propargyl, 2-(or 3-)butynyl, 2-(or 3- or 4-)pentynyl, 2-(or 3- or 4- or 5-)hexynyl, and the like, in which the preferred one is $C_2-C_5$alkynyl.

Suitable "lower alkoxymethyl" group may include a methyl group substituted by straight or branched lower alkoxy such as methoxymethyl, ethoxymethyl, propoxymethyl, isopropoxymethyl, pentyloxymethyl, hexyloxymethyl, and the like, in which the preferred one is $C_1-C_3$alkoxymethyl.

Suitable "lower alkylthiomethyl" group may include a methyl group substituted by straight or branched lower alkylthio such as methylthiomethyl, ethylthiomethyl, propylthiomethyl, isobutylthiomethyl, pentylthiomethyl, hexylthiomethyl, and the like, in which the preferred one is $C_1$–$C_3$alkylthiomethyl.

Suitable "lower alkenylthiomethyl" group may include a methyl group substituted by straight or branched lower alkenylthio such as vinylthiomethyl, 1-propenylthiomethyl, allylthiomethyl, 2-methyl-2-propenylthiomethyl, 1-(or 2- or 3-)butenylthiomethyl, 1-(or 2- or 3- or 4-)-pentenylthiomethyl, 1-(or 2- or 3- or 4-)hexenylthiomethyl, and the like, in which the preferred one is $C_2$–$C_5$alkenylthiomethyl.

Suitable "protected amino group" may include an amino group substituted by a conventional amino-protective group which is used in penicillin and cephalosporin compounds, for example, acyl as mentioned below, mono- (or di or tri)phenyl(lower)alkyl (e.g. benzyl, benzhydryl, trityl, etc.), lower alkoxycarbonyl(lower)alkylidene or its enamine tautomer (e.g. 1-methoxycarbonyl-1-propen-2-yl, etc.), di(lower)alkylaminomethylene (e.g. dimethylaminomethylene, etc.), etc.

Suitable "acyl" may include an aliphatic acyl, an aromatic acyl, a heterocyclic acyl and an aliphatic acyl substituted with aromatic or heterocyclic group(s).

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, tert-butoxycarbonyl, etc.), lower alkenoyl (e.g. acryloyl, methacryloyl, crotonoyl, etc.), ($C_3$–$C_7$)-cycloalkanecarbonyl (e.g. cyclohexanecarbonyl, etc.), amidino, and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclecarbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include phenyl(lower)alkanoyl (e.g. phenylacetyl, phenylpropionyl, phenylhexanoyl, etc.), phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro and the like, and preferable acyl having such substituents(s) may be mono (or di or tri)halo(lower)alkanoyl (e.g. chloroacetyl, bromoacetyl, dichloroacetyl, trifluoroacetyl, etc.), mono (or di or tri)halo(lower)alkoxycarbonyl (e.g. chloromethoxycarbonyl, dichloromethoxycarbonyl, 2,2,2-tri-chloroethoxycarbonyl, etc.), nitro (or halo or lower alkoxy)phenyl(lower)alkoxycarbonyl (e.g. nitrobenzyloxycarbonyl, chlorobenzyloxycarbonyl, methoxybenzyloxycarbonyl, etc.), and the like.

Suitable "protected carboxy group" may include an esterified carboxy group which is conventionally used in penicillin or cephalosporin compounds at their 3rd or 4th position thereof.

Suitable "ester moiety" in "esterified carboxy group" may include lower alkyl ester (e.g. methyl ester, ethyl ester, propyl ester, isopropyl ester, butyl ester, isobutyl ester, t-butyl ester, pentyl ester, tertpentyl ester, hexyl ester, etc.), lower alkenyl ester (e.g. vinyl ester, allyl ester, etc.), lower alkynyl ester (e.g. ethynyl ester, propynyl ester, etc.), lower alkoxy(lower)alkyl ester (e.g. methoxymethyl ester, ethoxymethyl ester, isopropoxymethyl ester, 1-methoxyethyl ester, 1-ethoxyethyl ester, etc.), lower alkylthio(lower)alkyl ester (e.g. methylthiomethyl ester, ethylthiomethyl ester, ethylthioethyl ester isopropylthiomethyl ester, etc.), amino- and carboxy-substituted lower alkyl ester (e.g. 2amino-2-carboxyethyl ester, 3-amino-3-carboxypropyl ester, etc.), protected amino and protected carboxy substituted lower alkyl ester such as lower alkoxycarbonylamino and mono-(or di or tri)phenyl(lower)alkoxycarbonyl substituted lower alkyl ester (e.g. 2-tert-butoxycarbonylamino-2-benzhydryloxycarbonylethyl, 3-tert-butoxycarbonylamino-3-benzhydryloxycarbonylpropyl, etc.), mono(or di or tri)halo(lower)alkyl ester (e.g. 2-iodoethyl ester, 2,2,2-trichloroethyl ester, etc.), lower alkanoyloxy(lower)alkyl ester (e.g. acetoxymethyl ester, propionyloxymethyl ester, butyryloxymethyl ester, isobutyryloxymethyl ester, valeryloxymethyl ester, pivaloyloxymethyl ester, hexanoyloxymethyl ester, 2-acetoxyethyl ester, 2-propionyloxyethyl ester, 1-acetoxypropyl ester, etc.), lower alkanesulfonyl(lower)alkyl ester (e.g. mesylmethyl ester, 2-mesylethyl ester, etc.), mono(or di or tri)phenyl(lower)alkyl ester which may have one or more suitable substituent(s) (e.g. benzyl ester, 4-methoxybenzyl ester, 4-nitrobenzyl ester, phenethyl ester, benzhydryl ester, trityl ester, bis(methoxyphenyl)methyl ester, 3,4-dimethoxybenzyl ester, 4-hydroxy-3,5-di-t-butylbenzyl ester, etc.), aryl ester which may have one or more suitable substituents (e.g. phenyl ester, tolyl ester, t-butylphenyl ester, xylyl ester, mesityl ester, cumenyl ester, salicyl ester, etc.), heterocyclic ester (e.g. phthalidyl ester, etc.) and the like.

Suitable "lower alkylene" group may include straight or branched one such as methylene, ethylene, trimethylene, propylene, tetramethylene, hexamethylene, and the like, in which the preferred one is $C_1$–$C_2$ alkylene and the most preferred one is methylene.

Suitable "heterocyclic" group may include saturated or unsaturated, monocyclic or polycyclic heterocyclic group containing at least one hetero-atom such as an oxygen, sulfur, nitrogen atom and the like. And, especially preferable heterocyclic group may be heterocyclic group such as unsaturated 3 to 8-membered(more preferably 5 or 6-membered)heteromonocyclic group containing 1 to 4 nitrogen atom(s), for example, pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1, 2,3-triazolyl, etc.), tetrazolyl (e.g. 1H-tetrazolyl, 2H-tetrazolyl, etc.) etc.;

saturated 3 to 8-membered(more preferably 5 to 6-membered)heteromonocyclic group containing 1 to 4 nitrogen atom(s), for example, pyrrolidinyl, imidazolidinyl, piperidino, piperazinyl, etc.:

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;

unsaturated 3 to 8-membered(more preferably 5 to 6-membered)heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, etc..;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

Thus defined heterocyclic group may optionally be substituted by one to ten, same or different, suitable substituent(s) such as: lower alkyl (e.g. methyl, ethyl, etc.); lower alkoxy (e.g. methoxy, ethoxy, propoxy, etc.); lower alkylthio (e.g. methylthio, ethylthio, etc.); lower alkylamino (e.g. methylamino, etc.); cyclo(lower)alkyl (e.g. cyclopentyl, cyclohexyl, etc.); cyclo(lower)alkenyl (e.g. cyclohexenyl; cyclohexadienyl, etc.); hydroxy; halogen (e.g. chloro, bromo, etc.); amino; protected amino as aforementioned; cyano; nitro; carboxy; protected carboxy as aforementioned; sulfo; sulfamoyl; imino; oxo; amino(lower)alkyl (e.g. aminomethyl, aminoethyl, etc.); and the like.

Suitable "lower alkoxycarbonyl(lower)alkyl" group may include ethoxycarbonylmethyl, propoxycarbonylmethyl, 1- or 2-ethoxycarbonylethyl, and the like.

Suitable "lower alkoxycarbonyl" moiety may include ethoxycarbonyl, propoxycarbonyl, and the like.

Suitable "halogen" may include chloro, bromo, iodo, and the like.

Suitable "conventional group which is capable to be replaced by the residue (—S—$R^b$) of the compound of the formula: HS—$R^b$" may include halogen as exemplified above.

Suitable "trihalomethyl" may include trichloromethyl, and the like.

Particularly, the preferred embodiment of the symbols "$R^1$—A—", "$R^2$" and "$R^3$" of the object compounds (I) can be represented as follows.

The symbol "$R^1$—A—" can be represented by the formulae:

① $R^1-\underset{\underset{OR^6}{\overset{\|}{N}}}{C}-$ , in which $R^1$ is a group of the formula:

$R^5 \text{—[thiazole]—}$ (more preferably $R^5 \text{—[thiazole]—}$)

wherein $R^5$ is amino or acylamino [more preferably lower alkanamido (e.g. formamido, acetamido, propionamido, etc.) or mono- or di- or trihalo(lower)alkanamido (e.g. chloroacetamido, dichloroacetamido, trifluoroacetamido, etc.)], $R^6$ is lower alkyl (e.g. methyl, ethyl, propyl, isopropyl, butyl, pentyl, hexyl, etc.), carboxy(lower)alkyl (e.g. carboxymethyl, 1- or 2-carboxyethyl, 1- or 2- or 3-carboxypropyl, etc.), or esterified carboxy(lower)alkyl [more preferably lower alkoxycarbonyl(lower)alkyl (e.g. methoxycarbonylmethyl, ethoxycarbonylmethyl, tert-butoxycarbonylmethyl, tert-butoxycarbonylethyl, etc.) or mono- or di- or triphenyl(lower)alkoxycarbonyl(lower)alkyl (e.g. benzyloxycarbonylmethyl, benzhydryloxycarbonylmethyl, benzhydryloxycarbonylethyl etc.)]; or ② $R^1$—A—, in which $R^1$ is a group of the formula:

$R^5 \text{—[thiazole]—}$ (more preferably $R^5 \text{—[thiazole]—}$)

wherein $R^5$ is amino or acylamino [more preferably lower alkanamido (e.g. formamido, acetamido, propionamido, etc.)], and A is methylene, aminomethylene, acylaminomethylene [more preferably lower alkoxycarbonylaminomethylene (e.g. methoxycarbonylaminomethylene, ethoxycarbonylaminomethylene, tert-butoxycarbonylaminomethylene, etc.)], hydroxymethylene or carbonyl; or ③ $R^1$—A—, in which $R^1$ is a group of the formula:

$R^4SO_2NH\text{—[phenyl]}$ (more preferably R⁴SO₂NH—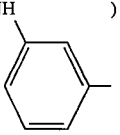)

wherein R⁴ is lower alkyl (e.g. methyl, ethyl, propyl, isopropyl, butyl, pentyl, etc.), and
A is aminomethylene or acylaminomethylene [more preferably lower alkoxycarbonylaminomethylene (e.g. methoxycarbonylaminomethylene, ethoxycarbonylaminomethylene, tert-butoxycarbonylaminomethylene, etc.)].

The symbol "R²" can be represented by: lower alkoxymethyl (e.g. methoxymethyl, ethoxymethyl, propoxymethyl, isopropoxymethyl, etc.); lower alkylthiomethyl (e.g. methylthiomethyl, ethylthiomethyl, propylthiomethyl, isopropylthiomethyl, etc.); or lower alkenylthiomethyl (e.g. vinylthiomethyl, allylthiomethyl, butenylthiomethyl, etc.).

The symbol "R³" can be represented by: carboxy or esterified carboxy [more preferably lower alkoxycarbonyl (e.g. methoxycarbonyl, ethoxycarbonyl, tert-butoxycarbonyl, etc.) or mono- or di- or triphenyl(lower)-alkoxycarbonyl (e.g. benzyloxycarbonyl, benzhydryloxycarbonyl, phenethyloxycarbonyl, etc.)].

The processes 1 to 13 for the preparation of the object compounds (I) of the present invention are explained in detail in the following.

(1) Process 1:

The compounds (I) or a salt thereof can be prepared by reacting the compound (II) or its reactive derivative at the amino group or a salt thereof with the compound (III) or its reactive derivative at the carboxy group or a salt thereof.

Suitable salts of the starting compounds (II) and (III) may include the same ones as illustrated for the compounds (I).

Suitable reactive derivative at the carboxy group of the compound (II) may include a conventional one, for example, a silyl derivative formed by the reaction of the compound (II) with a silyl compound such as bis(trimethylsilyl)acetamide, trimethylsilylacetamide, etc.; isocyanate; isothiocyanate; Schiff's base or its tautomeric enamine type isomer formed by the reaction of the amino group with a carbonyl compound such as an aldehyde compound (e.g. acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc.) or a ketone compound (e.g. acetone, methyl ethyl ketone, methyl isobutyl ketone, acetylacetone, ethyl acetoacetate, etc.), and the like.

Suitable reactive derivative of the compound (III) may include, for example, an acid halide, an acid anhydride, an activated amide, an activated ester, and the like, and preferably an acid chloride and acid bromide; a mixed acid anhydride with an acid such as substituted phosphoric acid (e.g. dialkylphosphoric acid, phenylphosphoric acid, diphenylphosphoric acid, dibenzylphosphoric acid, halogenated phosphporic acid, etc.), dialkylphosphorous acid, sulfurous acid, thiosulfuric acid, sulfuric acid, alkyl carbonate (e.g. methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.), a symmetrical acid anhydride; an activated acid amide with a heterocyclic compound containing imino function such as imidazole, 4-substituted imidazole, dimethylpyrazole, triazole or tetrazole; an activated ester (e.g. p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

Additionally, as a reactive derivative of the compound (III), wherein A is aminomethylene, the compound of the following formula can also be used.

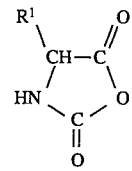

(wherein R¹ is as defined above)

The suitable reactive derivative can optionally be selected from the above according to the kinds of the compounds (II) and (III) to be used practically.

This reaction can be carried out in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), trialkylamine (e.g. triethylamine, etc.), pyridine compound (e.g. pyridine, lutidine, picoline, etc.), quinoline, and the like.

In case that the compound (III) is used in a form of the free acid or a salt in this reaction, the reaction is preferably carried out in the presence of a condensing agent such as a carbodiimide compound [e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2-methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to as so-called "Vilsmeier reagent") formed by the reaction of an amide compound such as dimethylformamide, N-methylformamide or the like with a halogen compound such as thionyl chloride, phosphoryl chloride, phosgene or the like.

The reaction is usually carried out in a conventional solvent which does not adversely influence the reaction such as water, acetone, dioxane, acetonitrile, chloroform, benzene, methylene chloride, ethylene chloride, tetrahydrofuran, ethyl acetate, N,N-dimethylformamide, pyridine, hexamethylphosphoramide, etc., or a mixture thereof.

Among these solvents, hydrophilic solvents may be used in a mixture with water.

The reaction temperature is not critical and the reaction is usually carried out under cooling to warming.

(2) Process 2:

The compound (I-b) or a salt thereof can be prepared by subjecting the compound (I-a) or a salt thereof to removal reaction of the amino-protective group in $A^1$.

Suitable method for this removal reaction may include conventional one such as hydrolysis, reduction and the like.

(i) For Hydrolysis:

Hydrolysis is preferably carried out in the presence of an acid.

Suitable acid may be an inorganic acid (e.g. hydrochloric acid, hydrobromic acid, sulfuric acid, etc.), an organic acid (e.g. formic acid, acetic acid, trifluoroacetic acid, propionic acid, benzenesulfonic acid, p-toluenesulfonic acid, etc.), an acidic ion-exchange resin and the like. In case that trifluoroacetic acid is used in this reaction, the reaction is preferably carried out in the presence of cation trapping agents (e.g. anisole, etc.).

The acid suitable for this hydrolysis can be selected according to the kinds of the protective group to be removed, for example, this hydrolysis can preferably be applied to the amino-protective group for $A^1$ such as substituted or unsubstituted lower alkoxycarbonyl, substituted or unsubstituted lower alkanoyl.

The hydrolysis is usually carried out in a conventional solvent which does not adversely influence the reaction such as water, methanol, ethanol, propanol, tetrahydrofuran, N,N-dimethylformamide, dioxane or a mixture thereof, and further the above-mentioned acids can also be used as a solvent when they are in liquid.

The reaction temperature of this hydrolysis is not critical, and the reaction is usually carried out under cooling to at somewhat elevated temperature.

(ii) For Reduction:

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction manner can be selected according to the kinds of the protective group to be removed, for example, the chemical reduction can preferably be applied to the amino-protective group for $A^1$ such as halo(lower)alkoxycarbonyl and the like, and catalytic reduction can preferably be applied to that such as substituted or unsubstituted ar(lower)alkoxycarbonyl, and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

The present invention includes, within the scope of the invention, cases that the protected amino group in $R^1$ and/or the protected carboxy group for $R^3$ are transformed into free amino group and/or free carboxy group, respectively during the reaction.

(3) Process 3:

The compound (I-d) or a salt thereof can be prepared by subjecting the compound (I-c) or a salt thereof to removal reaction of the amino-protective group in $R_a^1$.

This reaction is carried out by a conventional method such as hydrolysis, reduction, and the like.

The method of hydrolysis and reduction, and the reaction conditions (e.g. reaction temperature, solvent, etc.) are substantially the same as those illustrated for the removal reaction of the amino-protective group of the compound (I-a) in Process 2, and therefore are to be referred to said explanation.

The present invention includes, within the scope of the invention, cases that the protected amino group in A and/or the protected carboxy group(s) for $R^3$ and A are transformed into free amino group and/or free carboxy group, respectively during the reaction.

(4) Process 4:

The compound (I-f) or a salt thereof can be prepared by subjecting the compound (I-e) or a salt thereof to removal reaction of the carboxy-protective group for $R_a^3$.

This reaction is carried out by a conventional method such as hydrolysis, reduction, and the like.

The method of hydrolysis and reduction, and the reaction conditions (e.g. reaction temperature, solvent, etc.) are substantially the same as those illustrated for the removal reaction of the amino-protective group of the compound (I-a) in Process 2, and therefore are to be referred to said explanation.

The present invention includes, within the scope of the invention, cases that the protected amino group(s) in $R^1$ and A and/or the protected carboxy group in A are transformed into free amino group(s) and/or a free carboxy group, respectively, during the reaction.

(5) Process 5:

The compound (I-e) or a salt thereof can be prepared by introducing a carboxy-protective group into the compound (I-f) or a salt thereof.

The introducing agent of a carboxy-protective group to be used in this reaction may include a conventional esterifying agent such as an alcohol or its reactive equivalent (e.g. halide, sulfonate, sulfate, diazo compound, etc.), and the like.

This reaction can also be carried out in the presence of a base, and suitable examples thereof are the same as those given in the explanation of Process 1, and can preferably be carried out in the presence of metal iodide (e.g. sodium iodide, etc.).

This reaction is usually carried out in a conventional solvent which does not adversely influence the reaction such as N,N-dimethylformamide, tetrahydrofuran, dioxane, methanol, ethanol, etc., or a mixture thereof.

The reaction temperature is not critical, and the reaction is usually carried out under cooling to at somewhat elevated temperature.

In case that the alcohol is used as the introducing agent of a carboxy-protective group, the reaction can be carried out in the presence of a condensing agent as illustrated in Process 1.

(6) Process 6:

The compound (I-h) or a salt thereof can be prepared by reducing the compound (I-g) or a salt thereof.

The reduction can be carried out by a conventional method such as reduction using a reducing agent, catalytic reduction, and the like.

Suitable reducing agent may include a conventional one used for conversion of a carbonyl group to a hydroxymethyl group such as metal borohydride, for example, alkali borohydride (e.g. sodium borohydride, potassium borohydride, sodium cyanoborohydride, etc.), lithium aluminum hydride, etc.; diborane; and the like.

The catalyst to be used in the catalytic reduction may include the same ones as exemplified for the reduction in Process 2.

This reaction is usually carried out in a conventional solvent which does not adversely influence the reaction such as water, methanol, ethanol, tetrahydrofuran, dioxane; etc., or a mixture thereof.

The reaction temperature is not critical and the reaction is usually carried out under cooling to warming.

(7) Process 7:

The compound (I-i) or a salt thereof can be prepared by reacting the compound (IV) or a salt thereof with the compound (V).

Suitable salts of the starting compound (IV) may include the same salts with a base for the compounds (I).

This reaction is usually carried out in a conventional solvent which does not adversely influence the reaction such as ethyl acetate, methylene chloride, chloroform, carbon tetrachloride, tetrahydrofuran, dioxane, water, etc., or a mixture thereof.

The reaction temperature is not critical and the reaction is usually carried out under cooling to warming.

(8) Process 8:

The compound (I-l) or a salt thereof can be prepared by subjecting the compound (I-k) or a salt thereof to removal reaction of the carboxy-protective group in $A^6$.

This reaction is carried out by a conventional method such as hydrolysis, reduction, and the like.

The method of hydrolysis and reduction, and the reaction conditions (e.g. reaction temperature, solvent, etc.) are substantially the same as those illustrated for the removal reaction of the amino-protective group of the compound (I-a) in Process 2, and therefore are to be referred to said explanation.

The present invention includes, within the scope thereof, cases that the protected amino group in $R^1$ and/or the protected carboxy group in $R^3$ are transformed into free amino group and/or free carboxy group, respectively during the reaction.

(9) Process 9:

The compound (I-n) or a salt thereof can be prepared by subjecting the compound (I-m) or a salt thereof to removal reaction of the amino- and carboxy-protective groups in $R_b^3$.

This reaction is carried out by a conventional method such as hydrolysis, reduction, and the like.

The method of hydrolysis and reduction, and the reaction conditions (e.g. reaction temperature, solvent, etc.) are substantially the same as those illustrated for removal reaction of the amino-protective group of the compound (I-a) in Process 2, and therefore are to be referred to said explanation.

In this reaction, the amino- and carboxy-protective groups can be removed separately or at a time.

(10) Process 10:

The compound (I-p) or a salt thereof can be prepared by subjecting the compound (I-o) or a salt thereof to removal reaction of the amino- and carboxy-protective groups in $A^8$.

This reaction is carried out by a conventional method such as hydrolysis, reduction, and the like.

The method of hydrolysis and reduction, and the reaction conditions (e.g. reaction temperature, solvent, etc.) are substantially the same as those illustrated for removal reaction of the amino-protective group of the compound (I-a) in Process 2, and therefore are to be referred to said explanation.

In this reaction, the amino- and carboxy-protective groups can be removed separately or at a time.

(11) Process 11:

The compound (I-k) or a salt thereof can be prepared by introducing a carboxy-protective group into the compound (I-l) or a salt thereof.

This reaction is carried out by substantially the same method as that illustrated for introducing the carboxy-protective group into the compound (I-f) in Process 5, and therefore, the reaction conditions (e.g. reaction temperature, solvent, etc.) are to be referred to said explanation.

(12) Process 12:

The compound (I-r) or a salt thereof can be prepared by reacting the compound (I-q) or a salt thereof with the compound (VII).

This reaction is usually carried out in a conventional solvent which does not adversely influence the reaction such as tetrahydrofuran, dioxane, water, etc., or a mixture thereof.

The reaction temperature is not critical, and the reaction is usually carried out at ambient temperature to under heating.

(13) Process 13:

The compound (I-s) or a salt thereof can be prepared by reacting the compound (I-r) or a salt thereof with a base.

Suitable base used in this Process may include the same ones as those exemplified in Process 1.

This reaction is usually carried out in a conventional solvent which does not adversely influence the reaction such as water, methanol, ethanol, etc., or a mixture thereof.

The reaction temperature is not critical, and the reaction is usually carried out under cooling to warming.

The object compounds (I) obtained according to the Processes 1 to 13 as explained above can be isolated and purified in a conventional manner, for example, extraction, precipitation, fractional crystallization, recrystallization, chromatography, and the like.

Processes A to F for the preparation of the starting compounds (II-d), (II-g), (III-b) to (III-e), (III-g), (III-l), (IV) and (XIV-c) are explained in detail in the following.

Process A-1:

The compound (II-b) or a salt thereof can be prepared by reacting the compound (II-a) or a salt thereof with the compound (VIII) or its reactive derivative at the mercapto group.

Suitable salts of the compounds (II-a) and (II-b) may include the same salts with a base as exemplified for the compounds (I).

Suitable "reactive derivative at the mercapto group" of the compound (VIII) may include salts with a base as exemplified for the compounds (I).

This reaction is preferably carried out in the presence of a base and suitable examples thereof are the same as those given in the explanation of Process 1.

The reaction is usually carried out in a conventional solvent which does not adversely influence the reaction such as N,N-dimethylformamide, dimethylsulfoxide, methanol, ethanol, chloroform, etc., or a mixture thereof.

The reaction temperature is not critical and the reaction is usually carried out at ambient temperature to under warming.

Process A-2:

The compound (II-c) or a salt thereof can be prepared by reducing the compound (II-b) or a salt thereof.

Suitable salts of the compound (II-c) may include the same salts with a base as exemplified for the compounds (I).

The reducing agent to be used in this reaction may include a conventional one used for conversion of a sulfinyl group to a thio group such as phosphorus halide (e.g. phosphorus trichloride, phosphorus pentachloride, etc.); stannous halide (e.g. stannous chloride, etc.); silicon halide (e.g. silicon tetrachloride, etc.); excess amount of acid halide such as lower alkanoyl halide (e.g. acetyl bromide, acetyl chloride, etc.); combination of alkali metal halide (e.g. sodium iodide, etc.) and acid anhydride such as halo(lower)alkanoic anhydride (e.g. trifluoroacetic anhydride, etc.); and the like.

The reaction is usually carried out in the presence of an acid scavenger such as lower alkene (e.g. 2-methyl 2-butene, etc.), lower alkylene oxide (e.g. ethylene oxide, propylene oxide, etc.) and the like.

The reaction is usually carried out in a conventional solvent which does not adversely influence the reaction such as chloroform, methylene chloride, tetrahydrofuran, benzene, etc., or a mixture thereof.

The reaction temperature is not critical and the reaction is usually carried out under cooling to warming.

Process A-3:

The compound (II-d) or a salt thereof can be prepared by subjecting the compound (II-c) or a salt thereof to removal reaction of the amino-protective group for $R^a$.

Suitable salts of the compound (II-d) may include the same ones as exemplified for the compounds (I).

Suitable method for this removal reaction may include conventional one such as a combined method comprising iminohalogenation and iminoetherification, optionally followed by hydrolysis, and the like.

The first and second steps of this method are preferably carried out in an anhydrous solvent. Suitable solvent for the first step (i.e. iminohalogenation) is an aprotic solvent such as methylene chloride, chloroform, diethyl ether, tetrahydrofuran, dioxane, etc., and for the second step (i.e. iminoetherification) is usually the same as those in the above first step. These two steps are usually conducted under cooling. These two steps and the last step (i.e. hydrolysis step) are most preferably conducted in one-batch system.

Suitable iminohalogenating agents include a halogenating agent such as phosphorus halo compound (e.g. phosphorus trichloride, phosphorus pentachloride, phosphorus tribromide, phosphorus pentabromide, phosphorus oxychloride, etc.), thionyl chloride, phosgene, and the like.

Suitable iminoetherifying agent may be an alcohol such as an alkanol (e.g. methanol, ethanol, propanol, isopropanol, butanol, etc.) or the corresponding alkanol having alkoxy (e.g. 2-methoxyethanol, 2-ethoxyethanol, etc.), and alkoxide of metal such as alkali metal, alkaline earth metal (e.g. sodium methoxide, potassium ethoxide, magnesium ethoxide, lithium methoxide, etc.), and the like.

Thus obtained reaction product is, if necessary, hydrolyzed in a conventional manner.

The hydrolysis is preferably carried out at ambient temperature or under cooling, and proceeds simply pouring the reaction mixture into water or a hydrophilic solvent such as alcohol (e.g. methanol, ethanol, etc.) moistened or admixed with water, and if necessary, with addition of an acid or base as exemplified in Processes 1 and 2.

Process B-1:

The compound (III-b) can be prepared by reacting the compound (III-a) with the compound (IX) or a salt thereof.

Suitable salt of the compound (IX) may include the same one as exemplified for the compounds (I).

This reaction is preferably carried out in the presence of a base as exemplified in Process 1.

This reaction is usually carried out in a conventional solvent which does not adversely influence the reaction such as water, dioxane, tetrahydrofuran, etc., or a mixture thereof.

The reaction temperature is not critical and the reaction is usually carried out under cooling to warming.

Process B-2:

The compound (III-c) or a salt thereof can be prepared by reducing the compound (III-b).

Suitable salts of the compound (III-c) may include the same acid addition salt as exemplified for the compounds (I).

The reduction can be carried out by a conventional method such as chemical reduction, catalytic reduction, and the like.

The method of chemical reduction and catalytic reduction, and the reaction conditions (e.g. reaction temperature, solvent, etc.) are substantially the same as those illustrated for Process 2, and therefore are to be referred to said explanation.

Process B-3:

The compound (III-d) can be prepared by introducing an amino-protective group into the compound (III-c) or a salt thereof.

The introducing agent of an amino-protective group to be used in this reaction may include a conventional acylating agent such as the corresponding acid to the acyl group as aforementioned or its reactive derivative (e.g. acid halide, acid anhydride, etc.), 2-lower alkoxycarbonyloxyimino-2-phenylacetonitrile (e.g. 2-tert-butoxycarbonyloxyimino-2-phenylacetonitrile, etc.), alkyl ketone substituted by lower alkoxycarbonyl (e.g. lower alkyl acetoacetate, for example, methyl acetoacetate, etc., etc.), and the like.

This reaction is usually carried out in a conventional solvent which does not adversely influence the reaction such as water, methanol, ethanol, propanol, tetrahydrofuran, dioxane, etc., or a mixture thereof.

This reaction is preferably carried out in the presence of a base, and suitable examples thereof are the same as those given in the explanation of Process 1.

The reaction temperature is not critical and the reaction is usually carried out under cooling to warming.

Process B-4:

The compound (III-e) or a salt thereof can be prepared by subjecting the compound (III-d) to removal reaction of the carboxy-protective group.

Suitable salts of the compound (III-e) may include the same salts with a base as exemplified for the compounds (I).

This reaction is carried out by a conventional method such as hydrolysis, reduction, and the like.

The method of hydrolysis and reduction, and the reaction conditions (e.g. reaction temperature, solvent, etc.) are substantially the same as those illustrated for the removal reaction of the amino-protective group in Process 2, and therefore are to be referred to said explanation. Additionally, hydrolysis can be carried out in the presence of a base, and suitable examples thereof are the same as those in the explanation of Process 1.

Process B-5:

The compound (III-g) or a salt thereof can be prepared by subjecting the compound (III-f) or a salt thereof to removal reaction of the carboxy-protective group.

Suitable salts of the compound (III-f) may include the same acid addition salts as exemplified above, and those of the compound (III-g) may include the same salts as exemplified for the compounds (I).

The reaction is substantially the same as Process B-4, and therefore, the reaction method, reaction conditions (e.g. reaction temperature, solvent, etc.) are to be referred to said explanation.

Process B-6

The compound (III-e) or a salt thereof can be prepared by introducing an amino-protective group into the compound (III-g) or a salt thereof.

This reaction is substantially the same as Process B-3, and therefore, the reaction method and reaction conditions (e.g. reaction temperature, solvent, etc.) are to be referred to said explanation.

Process C:

The compound (IV) or a salt thereof can be prepared by reacting the compound (IV-a) or its reactive derivative at the amino group or a salt thereof with the compound (X) or its reactive derivative at the carboxy group or a salt thereof.

Suitable salts of the compound (IV-a) may include the same ones as exemplified for the compounds (I), and those of the compound (X) may include the same salts with a base as exemplified above.

The reaction is substantially the same method as Process 1, and accordingly, the method, reaction conditions (e.g. reaction temperature, solvent, base, etc.). are to be referred to said explanation.

In this process, carbonyl equivalents, for example, acetal of the compound (X), wherein $A^5$ is lower alkylene having oxo, can also be used in this reaction and such acetal can easily be transformed into the oxo group by a conventional method (e.g. hydrolysis, etc.) after the reaction.

Process D-1:

The compound (II-f) or a salt thereof can be prepared by reacting the compound (II-e) or a reactive derivative at the carboxy group or a salt thereof with lower alkanol substituted by protected amino and protected carboxy groups (XII).

Suitable salts of the compounds (II-e) and (II-f) may include the same ones as exemplified for the compounds (I).

Suitable reactive derivative at the carboxy group of the compound (II-e) may include the same ones as the compound (III) in Process 1.

This reaction is carried out by substantially the same method as that illustrated for introducing the carboxy-protective group into the compound (I-f) in Process 5, and therefore, the reaction conditions (e.g. reaction temperature, solvent, etc.) are to be referred to said explanation.

Process D-2:

The compound (II-g) or a salt thereof can be prepared by subjecting the compound (II-f) or a salt thereof to removal reaction of the amino-protective group for $R^a$.

Suitable salt of the compound (II-g) may include the same ones as exemplified for the compounds (I).

This reaction is carried out by substantially the same method as that illustrated for removal reaction of the amino-protective group of the compound (II-c) in Process A-3, and therefore, the reaction conditions (e.g. reaction temperature, solvent, etc.) are to be referred to said explanation.

Process E-1:

The compound (III-i) can be prepared by reacting the compound (III-h) with hydroxylamine or a salt thereof.

Suitable salt of hydroxylamine may include the same acid addition salt as exemplified for the compounds (I).

In case that the salt of hydroxylamine is used as the reagent, the reaction can usually be carried out in the presence of a base such as those illustrated in Process 1.

The reaction is usually carried out in a conventional solvent which does not adversely influence the reaction such as methanol, ethanol, etc., or a mixture thereof.

The reaction temperature is not critical and the reaction is usually carried out under cooling to warming.

Process E-2:

The compound (III-j) can be prepared by reacting the compound (III-i) with the compound (XIII) or a reactive derivative at the carboxy group or a salt thereof.

Suitable salt of the compound (XIII) may include the same salt with a base as exemplified for the compounds (I).

Suitable reactive derivative at the carboxy group of the compound (XIII) may include the same ones as illustrated for the compound (III) in Process 1.

This reaction is carried out by substantially the same method as Process 1, and therefore, the reaction conditions (e.g. reaction temperature, solvent, etc.) are to be referred to said explanation.

Process E-3:

The compound (III-k) or a salt thereof can be prepared by reacting the compound (III-j) or a salt thereof with ammonia.

Suitable salt of the compound (III-k) may include the same acid addition salt as exemplified for the compounds (I).

This reaction can be carried out in the absence of or in the presence of a solvent which does not adversely influence the reaction such as dioxane, etc., and the reaction is usually carried out in the absence of a solvent.

The reaction temperature is not critical and the reaction is usually carried out under cooling to warming.

In case that the compound (III-k) is one of the geometrical isomers, it can be transformed into the other isomer in a conventional manner.

Process E-4:

The compound (III-l) or a salt thereof can be prepared by subjecting the compound (III-k) or a salt thereof to removal reaction of the carboxy-protective group for $R^c$.

Suitable salt of the compound (III-l) may include the same ones as exemplified for the compounds (I).

This reaction is carried out by a conventional method such as hydrolysis, reduction, and the like.

The method of hydrolysis and reduction, and the reaction conditions (e.g. reaction temperature, solvent, etc.) are substantially the same as those illustrated for the removal reaction of the amino-protective group of the compound (I-a) in Process 2, and therefore are to be referred to said explanation.

Process F-1:

The compound (XIV-b) can be prepared by reacting the compound (XIV-a) or a reactive derivative at the hydroxy group with N-hydroxyphthalimide.

Suitable reactive derivative at the hydroxy group may include halide such as chloride, bromide, and the like.

This reaction is preferably carried out in the presence of a base as exemplified in Process 1.

In case that the compound (XIV-a) is used in a free form, the reaction can usually be carried out in the presence of a condensing agent as exemplified in Process 1.

This reaction is usually carried out in a conventional solvent which does not adversely influence the reaction such as tetrahydrofuran, N,N-dimethylformamide, etc., or a mixture thereof.

The reaction temperature is not critical and the reaction is usually carried out under cooling to warming.

Process F-2:

The compound (XIV-c) or a salt thereof can be prepared by subjecting the compound (XIV-b) to removal reaction of the phthaloyl group.

Suitable salt of the compound (XIV-c) may include the same acid addition salt as exemplified for the compounds (I).

This reaction is carried out by a conventional method such as hydrolysis, and the like.

The method of hydrolysis, and the reaction conditions (e.g. reaction temperature, solvent, etc.) are substantially the same as those illustrated for removal reaction of the aminoprotective group of the compound (I-a) in Process 2, and therefore are to be referred to said explanation.

The starting compounds (II-d), (II-g), (III-b) to (III-e), (III-l), (IV) and (XIV-c) thus prepared can be isolated in a conventional manner as mentioned for the object compounds of the present invention.

It is to be noted that, in the aforementioned reactions in Processes 1 to 13 and A to F or the post-treatment of the reaction mixture therein, in case that the starting or object compounds possess an optical and/or geometrical isomer(s), it may occasionally be transformed into the other optical and/or geometrical isomer(s), and such cases are also included within the scope of the present invention.

In case that the object compounds (I) have a free carboxy group or free amino group at the 4th or 7th position thereof, it may be transformed into its pharmaceutically acceptable salts by a conventional method.

The object compounds (I) and the pharmaceutically acceptable salts thereof of the present invention are novel and exhibit high antimicrobial activity, inhibiting the growth of a wide variety of pathogenic microorganisms including Gram-positive and Gram-negative microorganisms and are useful as antimicrobial agents, especially for oral administration.

Now in order to show the utility of the object compounds (I), the test data on the in vitro antimicrobial activity of some representative compounds (I) of this invention are shown in the following.

Test: In vitro Antimicrobial Activity

Test Compounds

No. 1 7-[2-(2-Aminothiazol-4-yl)-DL-glycolamido]-3-methylthiomethyl-3-cephem-4-carboxylic acid (hereinafter referred to as Compound A)

No. 2 7-[2-(3-Methanesulfonamidophenyl)-D-glycinamido]-3-methylthiomethyl-3-cephem-4-carboxylic acid trifluoroacetate (hereinafter referred to as Compound B)

No. 3 7-[2-(3-Methanesulfonamidophenyl)-D-glycinamido]-3-allylthiomethyl-3-cephem-4-carboxylic acid trifluoroacetate (hereinafter referred to as Compound C)

No. 4 7-[2-(3-Methanesulfonamidophenyl)-D-glycinamido]-3-methoxymethyl-3-cephem-4-carboxlic acid (hereinafter referred to as Compound D)

Test Method

In vitro Antimicrobial activity was determined by the two-fold agar-plate dilution method as described below.

One loopful of an overnight culture of each test strain in Tripticase-soy broth (approximately $10^8$ viable cells per ml) was streaked on heart infusion agar (HI-agar) containing graded concentrations of antimicrobial agents, and the minimal inhibitory concentration (MIC) was expressed in term of μg/ml after incubation at 37° C. for 20 hours.

| Test Compounds | Test Results 1 MIC (μg/ml) Microorganisms | |
|---|---|---|
| | Staphylococcus aureus 209P JC-1 | Batilus subtilis ATCC 6633 |
| A | 1.56 | 0.78 |
| B | 1.56 | 0.10 |
| C | 3.13 | 0.78 |
| D | 1.56 | 0.39 |

For therapeutic administration, the object compounds (I) and the pharmaceutically acceptable salts thereof of the present invention are used in the form of conventional pharmaceutical preparation which contains said compound, as active ingredients, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, magnesium stearate, terra alba, sucrose, corn starch, talc, stearic acid, gelatin, agar, pectin, peanut oil, olive oil, cacao butter, ethyleneglycol and the like.

While the dosage of the compounds (I) may vary from and also depend upon the age, conditions of the patient, a kind of diseases, a kind of the compounds (I) to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compounds (I) of the present invention may be used in treating diseases infected by pathogenic microorganisms.

The following examples are given for the purpose of illustrating the present invention.

Preparation of the starting compounds

Preparation 1

To a solution of benzhydryl 7-(2-phenylacetamido)-3-chloromethyl-3-cephem-4-carboxylate-1-oxide (25 g) in N,N-dimethylformamide (150 ml) were added triethylamine (6.42 ml) and 2-propene-1-thiol (8.0 ml), and the mixture was stirred at 25° C. for 3 hours.

The reaction mixture was poured into a saturated aqueous solution of sodium chloride (1.5 l), followed by collecting the precipitated solid by filtration, which was washed with water and diisopropyl ether, and then dried to give benzhydryl 7-(2-phenylacetamido)-3-allylthiomethyl-3-cephem-4-carboxylate-1-oxide (24.2 g).

I. R. (Nujol): 1775, 1715, 1644, 1170, 1030 cm$^{-1}$

NMR δ ppm (DMSO-d$_6$): 3.00 (2H, d, J=7 Hz), 3.6 (6H, m), 5.0 (1H, d, J=5 Hz), 5.90 (1H, dd, J=5 Hz, 8 Hz), 4.8–5.6 (3H, m), 7.00 (1H, s), 7.4 (15H, s), 8.40 (1H, d, J=8 Hz)

Preparation 2

Benzhydryl 7-(2-phenylacetamido)-3-methylthiomethyl-3-cephem-4-carboxylate-1-oxide (13.7 g) was obtained by reacting benzhydryl 7-(2-phenylacetamido)-3-chloromethyl-3-cephem-4-carboxylate-1-oxide (15 g) with 30% methanolic methanethiol (15 ml) in substantially the same manner as that of Preparation 1.

I. R. (Nujol): 3300, 1775, 1710, 1650, 1172, 1027 cm$^{-1}$

NMR δ ppm (DMSO-d$_6$): 1.80 (3H, s), 3.3–4.0 (6H, m), 5.02 (1H, d, J=5 Hz), 5.93 (1H, dd, J=5 Hz, 8 Hz), 7.02 (1H, s), 7.50 (15H, s), 8.40 (1H, d, J=8 Hz)

Preparation 3

Benzhydryl 7-(2-phenylacetamido)-3-ethylthiomethyl-3-cephem-4-carboxylate-1-oxide (14.1 g) was obtained by reacting benzhydryl 7-(2-phenylacetamido)-3-chloromethyl-3-cephem-4-carboxylate-1-oxide (15 g) with ethanethiol (4.05 ml) in substantially the same manner as that of Preparation 1.

I. R. (Nujol): 3280, 1776, 1708, 1647, 1172, 1015 cm$^{-1}$

NMR δ ppm (DMSO-$d_6$): 0.95 (3H, t, J=7 Hz), 2.28 (2H, q, J=7 Hz), 3.5–4.0 (6H, m), 5.02 (1H, d, J=5 Hz), 5.93 (1H, dd, J=5 Hz, 8.43 (1H, d, J=8 Hz)

Preparation 4

To a solution of benzhydryl 7-(2-phenylacetamido)-3-allylthiomethyl-3-cephem-4-carboxylate-1-oxide (26 g) in methylene chloride (500 ml) was added dropwise phosphorus trichloride (20 ml) at 5° C. with stirring, and the stirring was continued for an hour. The mixture was poured into a mixture of methylene chloride (200 ml) and water (400 ml), followed by separating out the organic layer, which was washed twice with an aqueous solution of sodium chloride (200 ml) and dried over anhydrous magnesium sulfate. After removal of the solvent, the residue was pulverized with diisopropyl ether to give benzhydryl 7-(2-phenylacetamido)-3-allylthiomethyl-3-cephem-4-carboxylate (22 g).

I. R. (Nujol): 1770, 1715, 1650 cm$^{-1}$

NMR (DMSO-$d_6$): 3.0 (2H, d, J=7 Hz), 3.6 (6H, m), 5.00 (1H, d, J=5 Hz), 5.67 (1H, dd, J=5 Hz, 8 Hz), 4.8–5.5 (3H, m), 6.90 (1H, s), 7.40 (15H, m), 9.10 (1H, d, J=8 Hz)

Preparation 5

To a solution of benzhydryl 7-(2-phenylacetamido)-3-methylthiomethyl-3-cephem-4-carboxylate-1-oxide (15.1 g) in methylene chloride (150 ml) was added 2-methyl-2-butene (5.7 ml), followed by adding dropwise acetyl bromide (5.2 ml) under ice-cooling and stirring for half an hour. After addition of water, the mixture was adjusted to pH about 5 with an aqueous solution of sodium bicarbonate, washed three times with an aqueous solution of sodium chloride, dried over anhydrous magnesium sulfate and then evaporated under reduced pressure to give benzhydryl 7-[2-phenylacetamido)-3-methylthiomethyl-3-cephem-4-carboxylate (13.5 g).

I.R. (Nujol): 3380, 1785, 1715, 1652 cm$^{-1}$

NMR δppm (DMSO-$d_6$): 1.83 (3H, s), 3.60 (4H, broad s), 3.66 (2H, broad s), 5.23 (1H, d, J=5 Hz), 5.75 (1H, dd, J=5 Hz, 8 Hz), 6.97 (1H, s), 7.43 (15H, s), 9.17 (1H, d, J=8 Hz)

Preparation 6

Benzhydryl 7-(2-phenylacetamido)-3-ethylthiomethyl-3-cephem-4-carboxylate (23 g) was obtained by reacting benzhydryl 7-(2-phenylacetamido)-3-ethylthiomethyl-3-cephem-4-carboxylate-1-oxide (30 g) with acetyl bromide (10.2 ml) in the presence of 2-methyl-2-butene (11.1 ml) in substantially the same manner as that of Preparation 5.

I.R. (Nujol): 3300, 1772, 1701, 1650 cm$^{-1}$

NMR δppm (DMSO-$d_6$): 1.00 (3H, t, J=7 Hz), 2.33 (2H, q, J=7 Hz), 3.56 (6H, broad s), 5.17 (1H, d, J=5 Hz), 5.76 (1H, dd, J=5 Hz, 8 Hz), 7.00 (1H, s), 9.13 (1H, d, J=8 Hz)

Preparation 7

To a suspension of phosphorus pentachloride (16.1 g) and pyridine (6.3 ml) in methylene chloride (100 ml) were added benzhydryl 7-(2-phenylacetamido)-3-allylthiomethyl-3-cephem-4-carboxylate (22 g) and methylene chloride (100 ml) at 5° C., and the mixture was stirred at the same temperature for an hour. After cooling to −20° C., methanol (10 ml) was added thereto, followed by stirring at −10° C. for half an hour. To this mixture was added water (10 ml) and stirred for 10 minutes. To the separated methylene chloride was added an aqueous solution of sodium bicarbonate until the pH value of the aqueous solution became 5.0, and the mixture was shaken. After separating out the organic layer, it was washed with an aqueous solution of sodium chloride, dried over anhydrous magnesium sulfate and evaporated to dryness. The residue obtained was pulverized with diisopropyl ether to give benzhydryl 7-amino-3-allylthiomethyl-3-cephem-4-carboxylate (6.5 g).

I.R. (Nujol): 1770, 1710 cm$^{-1}$

NMR δppm (DMSO-$d_6$): 2.93 (2H, d, J=7 Hz), 3.3–3.7 (4H, m), 5.00 (1H, d, J=5 Hz), 5.60 (1H, d, J=5 Hz), 4.5–5.6 (3H, m), 6.91 (1H, s), 7.5 (10H, m)

Preparation 8

Benzhydryl 7-amino-3-methylthiomethyl-3-cephem-4-carboxylate (5.0 g) was obtained by reacting benzhydryl 7-(2-phenylacetamido)-3-methylthiomethyl-3-cephem-4-carboxylate (13.5 ) with phosphorus pentachloride (7.74 g), pyridine (3 ml) and methanol (100 ml) in substantially the same manner as that of Preparation 7.

I.R. (Nujol): 1765, 1725 cm$^{-1}$

NMR δppm (DMSO-$d_6$): 1.81 (3H, s), 3.52 (2H, broad s), 3.60 (2H, broad s), 4.83, 5.13 (2H, ABq, J=5 Hz), 6.97 (1H, s), 7.40 (10H, s)

Preparation 9

Benzhydryl 7-amino-3-ethylthiomethyl-3-cephem-4-carboxylate (10.0 g) was obtained by reacting benzhydryl 7-(2-phenylacetamido)-3-ethylthiomethyl-3-cephem-4-carboxylate (23.0 g) with phosphorus pentachloride (12.90 g), pyridine (5.0 ml) and methanol (165 ml) in substantially the same manner as that of Preparation 7.

I.R. (Nujol): 1770, 1720 cm$^{-1}$

NMR δppm (DMSO-$d_6$): 0.96 (3H, t, J=7 Hz), 2.30 (2H, q, J=7 Hz), 3.50 (2H, broad s), 3.60 (2H, broad s), 4.80, 5.17 (2H, ABq, J=5 Hz), 7.00 (1H, s), 7.43 (10H, s)

Preparation 10

To a solution of diketene (1.3 ml) in methylene chloride (10 ml) was added dropwise a solution of bromine (1.24 g) in methylene chloride (10 ml) at −30° C. with stirring, and the stirring was continued at −20° C. for half an hour to prepare a solution of 4-bromoacetoacetyl bromide. This solution was added dropwise to a solution of benzhydryl 7-amino-3-methylthiomethyl-3-cephem-4-carboxylate (4.44 g) and trimethylsilylacetamide (5.46 g) in methylene chloride (100 ml) at −30° to −20° C. over a period of 5 minutes with stirring, and the stirring was continued at −10° C. for half an hour. After addition of water, the resultant mixture was adjusted to pH 7.5 with an aqueous solution of sodium bicarbonate, followed by separating out the organic layer, which was washed with water and an aqueous solution of sodium chloride, dried over anhydrous magnesium sulfate, and then evaporated to dryness to give benzhydryl 7-(4-bromoacetoacetamido)-3-methylthiomethyl-3-cephem-4-carboxylate (6.0 g).

IR (Nujol): 1770, 1710, 1625 cm$^{-1}$

NMR δppm (DMSO-$d_6$): 1.77 (3H, s), 3.6 (6H, m), 4.33 (2H, s), 5.15 (1H, d, J=4 Hz), 5.73 (1H, dd, J=4 Hz, 8 Hz), 6.86 (1H, s), 7.3 (10H, m), 9.1 (1H, d, J=8 Hz)

Preparation 11

To a solution of ethyl 2-(2-formamidothiazol-4-yl)-2-methoxyiminoacetic acid (syn isomer) (19 g) in methanol (200 ml) were added 50% formic acid (200 ml) and zinc (29 g), and the mixture was stirred at 5° to 10° C. for 6 hours. After filtration, the reaction mixture was evaporated, followed by dissolving the residue in water (150 ml). The resultant aqueous solution was adjusted to pH 6.5 with 4N aqueous solution of sodium hydroxide, followed by addition of ethanol (150 ml), 2-tert-butoxycarbonyloxyimino-2-phenylacetonitrile (18.2 g) and triethylamine (8.0 g). After stirring at ambient temperature for 24 hours, the reaction mixture was filtered, followed by removal of the organic solvent. The remained aqueous solution was washed with ethyl acetate, adjusted to pH 4 with 10% hydrochloric acid and then extracted with ethyl acetate. The extract was washed with an aqueous solution of sodium chloride, dried over anhydrous magnesium sulfate and evaporated to dryness under reduced pressure to give a residue, which was washed with diethyl ether to obtain N-tert-butoxycarbonyl-2-(2-formamidothiazol-4-yl) glycine (3.3 g).

IR (Nujol): 3250, 3180, 1720, 1670, 1640, 1540, 1510 cm$^{-1}$

NMR δppm (DMSO-d$_6$): 1.40 (9H, s), 5.18 (1H, d, J=8 Hz), 7.17 (1H, s), 8.43 (1H, s)

Preparation 12

Bromoacetic acid (10.45 g) was dissolved in methanol (30 ml). To the solution was added an equivalent volume of diphenyl diazomethane in ethyl acetate at 45° C., and the reaction mixture was stirred at the same temperature for an hour. The solution was washed with 5% aqueous sodium bicarbonate and a saturated aqueous sodium chloride, and then dried over magnesium sulfate. The solution was evaporated in vacuo to give an oily product. This oil was dissolved in N,N-dimethylformamide (60 ml). To the solution was added N-hydroxyphthalimide (11.7 g) and triethylamine (15.1 ml), and the reaction mixture was stirred at ambient temperature for an hour. The resultant mixture was poured into a saturated aqueous sodium chloride (500 ml). The precipitates were collected by filtration, washed with water, and then dissolved in methylene chloride (700 ml). The solution was washed with a saturated aqueous sodium chloride, dried over magnesium sulfate, and then evaporated under reduced pressure to give benzhydryl 2-phthalimidooxyacetate (20.4 g), mp 173°–175° C.

IR (Nujol): 1754, 1730 cm$^{-1}$

NMR δ ppm (CDCl$_3$,δ):4.93 (2H,s), 7.0 (1H,s), 7.3 (10H, s), 7.73 (4H,s).

Preparation 13

To a solution of benzhydryl 2-phthalimidooxyacetate (10 g) in methylene chloride (100 ml) was added a solution of hydrazine hydrate (6.08 g) in methanol (7 ml). The reaction mixture was stirred at ambient temperature for an hour. The precipitates were collected by filtration and washed with methylene chloride. The filtrate and the washings were combined, adjusted to pH 7.0 with conc. hydrochloric acid, and washed with a saturated aqueous sodium chloride, and then dried over magnesium sulfate. The solution was evaporated in vacuo to give benzhydryl 2-aminooxyacetate (6.0 g).

IR (film): 3320, 1750 cm$^{-1}$

NMR δ ppm (CDCl$_3$,δ): 4.33 (2H,s), 5.86 (2H, broad s), 7.00 (1H, s), 7.3 (10H,s)

Preparation 14

To a suspension of (2-formamidothiazol-4-yl)-glyoxylic acid (6.0 g) in water (60 ml) and pyridine (6 ml) was added a solution of benzhydryl 2-aminooxyacetate (9.0 g) in tetrahydrofuran (40 ml). The reaction mixture was stirred at ambient temperature for 3 hours. To the resultant solution was added ethyl acetate (200 ml). The separated organic layer was washed with 5% hydrochloric acid (100 ml), a saturated aqueous sodium bicarbonate and a saturated aqueous sodium chloride, and then dried over magnesium sulfate. The solvent was distilled off to give 2-(2-formamidothiazol-4-yl)-2-benzhydryloxycarbonylmethoxyiminoacetic acid (syn isomer) (13.0 g), mp 143°–151° C.

IR (Nujol): 3150, 1733, 1692 cm$^{-1}$

NMR δ ppm (DMSO-d6): 5.0 (2H, broad s), 6.97 (1H, s), 7.40 (20H, m), 7.56 (1H, s), 8.60 (1H, s), 12.77 (1H, broad s)

Preparation 15

To a solution of 2-benzhydryloxycarbonylmethoxyimino-2-(2-formamidothiazol-4-yl)acetic acid (syn isomer) (7.5 g) in tetrahydrofuran (40 ml) was added trifluoroacetic anhydride (7.9 g) at −16° C. for 10 minutes. To the reaction mixture was added triethylamine (5.3 ml) at −10° C., and then the mixture was stirred for 90 min at 0° to 5° C. To the above mixture were added ethyl acetate (100 ml) and water (100 ml), and adjusted to pH 7.5 with a saturated aqueous sodium bicarbonate. The aqueous layer was adjusted to pH 2.0 with conc. hydrochloric acid and extracted with ethyl acetate (200 ml). The organic layer was washed with a saturated aqueous sodium chloride and dried over magnesium sulfate. The solvent was removed by evaporation under reduced pressure to give an oil. n-Hexane was added to the oil and the precipitated substance was collected by filtration to give crystalline 2-benzhydryloxycarbonylmethoxyimino-2-[2-(2,2,2-trifluoroacetamido)thiazol-4-yl]acetic acid (syn isomer) (6.0 g), mp 178°–180° C.

IR (Nujol): 1752, 1726 cm$^{-1}$

NMR δ ppm (DMSO-d6): 4.98 (2H, s), 6.92 (1H, s), 7.32 (10H, m), 7.69 (1H, s)

Preparation of the object compounds

EXAMPLE 1

To a solution of N-tert-butoxycarbonyl-2-(3-methanesulfonamidophenyl)-D-glycine (3.3 g) and triethylamine (1.34 ml) in tetrahydrofuran (50 ml) was added dropwise a solution of ethyl chloroformate (0.91 ml) in tetrahydrofuran (10 ml) at −10° to −7° C. with stirring, and the stirring was continued at the same temperature for 40 minutes to give a solution of the activated acid. This solution was added dropwise to a solution of benzhydryl 7-amino-3-methylthiomethyl-3-cephem-4-carboxylate (3.0 g) in methylene chloride (100 ml) at −30° C. over a period of 5 minutes with stirring, and the stirring was continued at the same temperature for an hour. After addition of water, the reaction mixture was stirred for half an hour, followed by extracting with methylene chloride (100 ml). The extract was washed twice with 5% aqueous solution of sodium bicarbonate (50 ml) and an aqueous solution of sodium chloride, and then dried over anhydrous magnesium sulfate, followed by evaporation under reduced pressure to give benzhydryl 7-[N-tert-butoxycarbonyl-2-3-methanesulfonamidophenyl)-D-glycinamido]-3-methylthiomethyl-3-cephem-4-carboxylate (6.5 g).

I.R. (Nujol): 1780, 1710, 1680, 1152 cm$^{-1}$

NMR δ ppm (DMSO-d$_6$): 1.36 (9H, s), 1.76 (3H, s), 2.98 (3H, s), 3.3–3.8 (4H, m), 5.12 (1H, d, J=5 Hz), 5.73 (1H, dd, J=5 Hz, 8 Hz), 6.93 (1H, s), 7.1–7.4 (14H, m), 9.93 (1H, d, J=8 Hz)

EXAMPLE 2

Benzhydryl 7-[N-tert-butoxycarbonyl-2-(3-methanesulfonamidophenyl)-D-glycinamido]-3-ethylthiomethyl-3-cephem-4-carboxylate (5.4 g) was obtained by reacting benzhydryl 7-amino-3-ethylthiomethyl-3-cephem-4-carboxylate (3.08 g) with N-tert-butoxycarbonyl-2-(3-methanesulfonamidophenyl)-D-glycine (3.3 g) in substantially the same manner as that of Example 1.

I.R. (Nujol): 3250, 1780, 1700, 1530, 1490, 1455 cm$^{-1}$

NMR δ ppm (DMSO-d$_6$): 0.98 (3H, t, J=7 Hz), 1.38 (9H, s), 2.28 (2H, q, J=7 Hz), 2.97 (3H, s), 3.4–3.8 (4H, m), 5.12 (1H, d, J=5 Hz), 5.24 (1H, m), 5.73 (1H, dd, J=5 Hz, 7 Hz), 6.93 (1H, s), 7.0–7.7 (14H, m), 9.89 (1H, d, J=8 Hz), 10.43 (1H, s)

EXAMPLE 3

(1) To a suspension of tert-butyl 7-amino-3-methoxymethyl -3-cephem-4-carboxylate tosylate (13.1 g) in methylene chloride (200 ml) was added water (100 ml), followed by adjusting to pH about 6 with an aqueous solution of sodium bicarbonate. After separating out the methylene chloride layer, the remaining aqueous solution was extracted with methylene chloride (50 ml). The combined methylene chloride solution was washed with an aqueous solution of sodium chloride, dried over anhydrous magnesium sulfate and then treated with an activated charcoal, followed by evaporation under reduced pressure to give tert-butyl 7-amino-3-methoxymethyl-3-cephem-4-carboxylate (5.7 g).

I.R. (Nujol): 3370, 1760, 1740, 1710 cm$^{-1}$

NMR δ ppm (DMSO-$d_6$): 1.5 (9H, s), 2.3 (2H, broad s), 3.24 (3H, s), 3.51 (2H, s), 4.15 (2H, s), 4.8 (1H, d, J=5 Hz), 5.04 (1H, d, J=5 Hz)

(2) On the other hand, to a solution of N-tert-butoxycarbonyl-2-(3-methanesulfonamidophenyl)-D-glycine (8.89 g) and triethylamine (2.61 g) in dry tetrahydrofuran (95 ml) was added dropwise a solution of ethyl chloroformate (2.8 g) in dry tetrahydrofuran (25 ml) at −10° to −7° C. over a period of 10 minutes with stirring, and stirring was continued at the same temperature for 40 minutes to prepare a solution of the activated acid.

(3) To a solution of the compound (5.65 g) obtained according to Example 3-(1) in dry methylene chloride (190 ml) was added dropwise the solution of the activated acid prepared above at −30° C. over a period of 10 minutes with stirring, and the stirring was continued at the same temperature for an hour. After addition of water (100 ml), the reaction mixture was stirred for half an hour. The methylene chloride layer was separated out therefrom and the remaining aqueous solution was extracted with methylene chloride. The combined methylene chloride solution was washed twice with 5% aqueous solution of sodium bicarbonate (100 ml) and an aqueous solution of sodium chloride, dried over anhydrous magnesium sulfate, and then treated with an activated charcoal, followed by evaporation under reduced pressure to give tert-butyl 7-[N-tert-butoxycarbonyl-2-(3-methanesulfonamidophenyl)-D-glycinamido]-3-methoxymethyl-3-cephem-4-carboxylate (17.8 g).

I.R. (Nujol): 3250, 1780, 1710, 1680 cm$^{-1}$

NMR δppm (DMSO-$d_6$): 1.36 (9H, s), 1.46 (9s), 2.97 (3H, s), 3.18 (3H, s), 3.4 (2H, broad s), 4.07 (2H, broad s), 5.03 (1H, d, J=5 Hz), 5.24 (1H, d, J=8 Hz), 5.73 (1H, dd, J=5 Hz, 8 Hz), 6.93–7.43 (4H, m), 7.5 (1H, d, J=8 Hz), 9.16 (1H, d, J=8 Hz), 9.73 (1H, broad s), The compounds described in the following Examples 4 to 7 were obtained by reacting the corresponding 7-aminocephalosporanic acid derivative with 2-(3-methanesulfonamidophenyl)-D-glycine in substantially the same manner as that of Example 3.

EXAMPLE 4

7-[2-(3-Methanesulfonamidophenyl)-D-glycinamido]-3-methylthiomethyl-3-cephem-4-carboxylic acid.

I.R. (Nujol): 1758, 1687 (shoulder), 1666, 1144, 974 cm$^{-1}$

EXAMPLE 5

7-[2-(3-Methanesulfonamidophenyl)-D-glycinamido]-3-ethylthiomethyl-3-cephem-4-carboxylic acid.

I.R. (Nujol): 3500, 3150, 1780, 1685, 1460 cm$^{-1}$

EXAMPLE 6

7-[2-(3-Methanesulfonamidophenyl)-D-glycinamido]-3-methoxymethyl-3-cephem-4-carboxylic acid.

I.R. (Nujol): 3500, 3150, 1760, 1685 cm$^{-1}$

EXAMPLE 7

7-[2-(3-Methanesulfonamidophenyl)-D-glycinamido]-3-allylthiomethyl-3-cephem-4-carboxylic acid trifluoroacetate.

I.R. (Nujol): 1760, 1680, 1600, 1140 cm$^{-1}$

EXAMPLE 8

A mixture of benzhydryl 7-[N-tert-butoxycarbonyl-2-(3-methanesulfonamidophenyl)-D-glycinamido]-3-methylthiomethyl-3-cephem-4-carboxylate (6.5 g), anisole (5.0 ml) in trifluoroacetic acid (20 ml) was stirred at 25° C. for 15 minutes. After the reaction, the reaction mixture was added dropwise to diisopropyl ether (300 ml), and the precipitated solid was collected by filtration, washed with diisopropyl ether and then dissolved in a mixture of water (50 ml) and ethyl acetate (50 ml). After the aqueous layer was separated out, it was washed with ethyl acetate, followed by removal of ethyl acetate from the aqueous solution completely under reduced pressure. The resultant aqueous solution was adjusted to pH 3.8 with an aqueous solution of sodium bicarbonate and subjected to column chromatography using "Diaion HP-20" (90 ml). After washing with water (180 ml), elution was carried out with 30% isopropyl alcohol, and the fractions containing the desired compound were collected and lyophilized to give 7-[2-(3-methanesulfonamidophenyl)-D-glycinamido]-3-methylthiomethyl-3-cephem-4-carboxylic acid (4.8 g).

I.R. (Nujol): 1758, 1687 (shoulder), 1666, 1144, 974 cm$^{-1}$

NMR δppm (D$_2$O+DCl): 1.98 (3H, s), 3.15 (3H, s), 3.45 (2H, broad s), 3.56 (2H, broad s), 5.12 (1H, d, J=5 Hz), 5.30 (1H, s), 5.70 (1H, d, J=5 Hz), 7.45 (4H, s)

EXAMPLE 9

7-[2-(3-Methanesulfonamidophenyl)-D-glycinamido]-3-ethylthiomethyl-3-cephem-4-carboxylic acid (1.6 g) was obtained by reacting benzhydryl 7-[N-tert-butoxycarbonyl-2-(3-methanesulfonamidophenyl)-D-glycinamido]-3-ethylthiomethyl-3-cephem-4-carboxylate (3.7 g) with trifluoroacetic acid (7.4 ml) in the presence of anisole (7.4 ml) in substantially the same manner as that of Example 8, mp 188° C. (dec.).

I.R. (Nujol): 3500, 3150, 1780, 1685, 1460 cm$^{-1}$

NMR δppm (D$_2$O+DCl): 1.13 (3H, t, J=7 Hz), 2.48 (2H, q, J=7 Hz), 3.11 (3H, s), 3.3–3.8 (4H, m), 5.30 (1H, s), 5.65 (1H, d, J=5 Hz), 7.43 (4H, s)

EXAMPLE 10

To a solution of tert-butyl 7-[N-tert-butoxycarbonyl-2-(3-methanesulfonamidophenyl)-D-glycinamido]-3-methoxymethyl-3-cephem-4-carboxylate (15 g) in anisole (11.25 ml) was added dropwise trifluoroacetic acid (33.75 ml) below 15° C. over a period of 10 minutes with stirring, and the stirring was continued at 15° to 20° C. for half an hour. The reaction mixture was poured into diisopropyl ether (750 ml), followed by stirring at ambient temperature for 20 minutes. After the precipitated solid was collected by filtration and washed with diisopropyl ether, it was poured into a mixture of ethyl acetate (100 ml) and water (100 ml) and stirred for a while. The aqueous solution was separated out therefrom, and the remaining organic layer was extracted with water. The combined aqueous solution was concentrated under reduced pressure, and the concentrate was adjusted to pH about 3.8 with an aqueous solution of sodium bicarbonate, followed by subjecting to column chromatography using non-ionic adsorption resin "Diaion HP-20" (225 ml), which was washed with water (450 ml) and then eluted with 30% isopropyl alcohol. The fractions containing the desired compound were collected and evaporated under reduced pressure, and the residue was lyophilized to give 7-[2-(3-methanesulfonamidophenyl)-D-glycinamido]-3-methoxymethyl-3-cephem-4-carboxylic acid (4.45 g).

I.R. (Nujol): 3500, 3150, 1760, 1685 cm$^{-1}$

NMR δppm ($D_2O$+DCl): 3.13 (3H, s), 3.26 (3H, s), 3.42 (2H, q, J=18 Hz), 4.25 (2H, s), 5.06 (1H, d, J=5 Hz), 5.27 (1H, s), 5.73 (1H, d, J=5 Hz), 7.42 (4H, s)

EXAMPLE 11

Benzhydryl 7-amino-3-allylthiomethyl-3-cephem-4-carboxylate (3.3 g) and N-tert-butoxycarbonyl-2-(3-methanesulfonamidophenyl)-D-glycine (3.44 g) were treated in substantially the same manner at that of Example 1 to give an oily product (6.5 g). A mixture of this oil, trifluoroacetic acid (15 ml) and anisole (15 ml) was stirred at 20° C. for half an hour, followed by adding dropwise to diisopropyl ether. The presipitated solid was collected by filtration, washed with diisopropyl ether and then dissolved in a mixture of water (50 ml) and ethyl acetate (50 ml). The aqueous layer was separated out and washed with diethyl ether, followed by removal of the organic solvent therefrom completely. The resultant aqueous solution was lyophilized to give 7-[2-(3-methanesulfonamidophenyl)-D-glycinamido]-3-allylthiomethyl-3-cephem-4-carboxylic acid trifluoroacetate (2 g).

I.R. (Nujol): 1760, 1680, 1600, 1140 cm$^{-1}$

NMR δ ppm ($D_2O$+DCl): 3.20 (2H, m), 3.23 (3H, s), 3.6 (7H, m), 5.2 (1H, d, J=5 Hz), 5.45 (1H, s), 5.80 (1H, d, J=5 Hz), 7.55 (3H, m)

EXAMPLE 12

To a solution of benzhydryl 7-[4-bromoacetoacetamido)-3-methylthiomethyl-3-cephem-4-carboxylate (6.0 g) in tetrahydrofuran (30 ml) was added dropwise a solution of thiourea (0.85 g) and sodium bicarbonate (0.94 g) in tetrahydrofuran (30 ml) and water (24 ml) at 25° C. with stirring, and the stirring was continued at 28° to 30° C. for an hour. The reaction mixture was poured into a mixture of ethyl acetate (100 ml) and water (100 ml), followed by separating out the organic layer, which was washed twice with an aqueous solution of sodium chloride, dried over anhydrous magnesium sulfate and then evaporated to give benzhydryl 7-[2-(2-aminothiazol-4-yl) acetamido]-3-methylthiomethyl-3-cephem-4-carboxylate (4.0 g).

IR (Nujol): 1773, 1715, 1653 cm$^{-1}$

NMR δ ppm (DMSO-$d_6$): 1.85 (3H, s), 3.3–3.8 (6H, m), 5.25 (1H, d, J=5 Hz), 5.80 (1H, dd, J=5 Hz, 8 Hz), 6.32 (1H, s), 7.00 (1H, s), 7.43 (10H, s), 8.95 (1H, d, J=8 Hz)

EXAMPLE 13 tert-Butyl 7-amino-3-methoxymethyl-3-cephem-4-carboxylate tosylate (2.0 g) was dissolved in a mixture of acetone (40 ml) and a saturated aqueous solution of sodium bicarbonate (15 ml), and thereto was added dropwise a solution of the activated acid, which was prepared from 2-(2-formamidothiazol-4-yl)-2-methoxyiminoacetic acid (syn isomer) (1.06 g), phosphorus oxychloride (0.85 g) and N,N-dimethylformamide (0.41 g) in tetrahydrofuran (10 ml), at 0° to 5° C. over a period of 10 minutes. During the addition, the pH value of the reaction mixture was maintained at pH 7.0 to 7.5 with a saturated aqueous solution of sodium carbonate. After stirring for an hour, the reaction mixture was diluted with water (50 ml), followed by extracting twice with ethyl acetate. The combined extract was washed with 5% aqueous solution of sodium bicarbonate and water, dried and then evaporated to dryness under reduced pressure to give a residue, which was triturated with diethyl ether to obtain tert-butyl 7-[2-(2-formamidothiazol-4-yl)-2-methoxyiminoacetamido]-3-methoxymethyl-3-cephem-4-carboxylate (syn isomer) (1.14 g).

IR (Nujol): 3250, 3100, 1790, 1710, 1660 cm$^{-1}$

NMR δ ppm (DMSO-$d_6$): 1.49 (9H, s), 3.21 (3H, s), 3.28 (2H, broad s), 3.89 (3H, s), 4.1 (2H, s), 5.16 (1H, d, J=5 Hz), 5.80 (1H, dd, J=5 Hz, 8 Hz), 7.36 (1H, s), 8.48 (1H, s), 9.6 (1H, d, J=8 Hz), 12.66 (1H, broad s)

EXAMPLE 14 tert-Butyl 7-[2-(2-formamidothiazol-4-yl)-2-methoxyiminoacetamido]-3-methylthiomethyl-3-cephem-4-carboxylate (syn isomer) (0.91 g) was obtained by reacting tert-butyl 7-amino-3-methylthiomethyl-3-cephem-4-carboxylate (0.90 g) with 2-(2-formamidothiazol-4-yl)-2-methoxyiminoacetic acid (syn isomer) (0.85 g) according to the similar manner to that of Example 13.

IR (Nujol): 3250, 3050, 1780, 1690 cm$^{-1}$

NMR δ ppm (DMSO-$d_6$): 1.47 (9H, s), 1.97 (3H, s), 3.29 (2H, broad s), 3.55 (2H, ABq, J=13 Hz), 3.87 (3H, s), 5.21 (1H, d, J=5 Hz), 5.76 (1H, dd, J=5 Hz, 8 Hz), 7.38 (1H, s), 8.49 (1H, s), 9.66 (1H, d, J=8 Hz), 12.56 (1H, broad s)

The compounds described in the following Examples 15 to 17 were obtained by reacting the 7-aminocephalosporanic acid derivatives with the corresponding acid according to the similar manner to that of Example 13.

EXAMPLE 15

7-[2-(2-Aminothiazol-4-yl)acetamido]-3-methylthiomethyl-3-cephem-4-carboxylic acid IR (Nujol): 1763, 1654 cm$^{-1}$

EXAMPLE 16

7-[2-(2-Aminothiazol-4-yl)-2-methoxyiminoacetamido]-3-methoxymethyl-3-cephem-4-carboxylic acid hydrochloride (syn isomer)

IR (Nujol): 3300, 1780, 1720, 1660, 1640 cm$^{-1}$

EXAMPLE 17

7-[2-(2-Aminothiazol-4-yl)-2-methoxyiminoacetamido]-3-methylthiomethyl-3-cephem-4-carboxylic acid (syn isomer)

IR (Nujol): 3350, 1770, 1670 cm$^{-1}$

EXAMPLE 18

The mixture of benzhydryl 7-[2-(2-aminothiazol-4-yl)acetamido]-3-methylthiomethyl-3-cephem-4-carboxylate (3.3 g), trifluoroacetic acid (10 ml) and anisole (10 ml) in methylene chloride (10 ml) was stirred at 10° C. for an hour. After benzene (50 ml) was added to the reaction mixture, the trifluoroacetic acid therein was mixture, the trifluoroacetic acid therein was azeotropically removed under reduced pressure. The remained aqueous solution was poured into a mixture of ethyl acetate (100 ml) and water (100 ml), followed by adjusting to pH 7.5 with sodium bicarbonate. After separating out the aqueous solution, the organic solvent was removed therefrom by evaporation completely under reduced pressure, followed by adjusting to pH 3.0 with 10% hydrochloric acid. The precipitated solid was collected by filtration and then dried to give 7-[2-(2-aminothiazol-4-yl)acetamido]-3-methylthiomethyl-3-cephem-4-carboxylic acid (0.95 g).

IR (Nujol): 1763, 1654 cm$^{-1}$

NMR δ ppm (DMSO-d$_6$): 2.01 (3H, s), 3.48 (2H, s), 3.65 (4H, broad s), 5.17 (1H, d, J=5 Hz), 5.67 (1H, dd, J=5 Hz, 8 Hz), 6.38 (1H, s), 9.00 (1H, d, J=8 Hz)

EXAMPLE 19

To a cold suspension of tert-butyl 7-[2-(2-formamidothiazol-4-yl)-2-methoxyiminoacetamido]-3-methoxymethyl-3-cephem-4-carboxylate(syn isomer) (1.0 g) in methylene chloride (20 ml) were added trifluoroacetic acid (4.4 g) and anisole (0.2 ml), and the mixture was gradually warmed at 40° C., followed by stirring at 10° C. for 3 hours. After evaporation of the reaction mixture, to the residue was added ethyl acetate (20 ml), followed by extracting with an aqueous solution of sodium bicarbonate. The resultant aqueous solution was adjusted to pH 2.0 with diluted hydrochloric acid and then extracted with ethyl acetate. The extract was washed with a saturated aqueous solution of sodium bicarbonate, water and an aqueous solution of sodium chloride in turn, dried and then evaporated to dryness under reduced pressure. The residue was stirred for 30 minutes in diethyl ether, and the remained substance was collected by filtration to give 7-[2-(2-formamidothiazol-4-yl)-2-methoxyiminoacetamido]-3-methoxymethyl-3-cephem-4-carboxylic acid (syn isomer) (0.56 g).

IR (Nujol): 3250, 1780, 1660 cm$^{-1}$

NMR δ ppm (DMSO-d$_6$): 3.22 (3H, s), 3.55 (2H, broad s), 3.90 (3H, s), 4.19 (2H, s), 5.17 (1H, d, J=5 Hz), 5.81 (1H, dd, J=5Hz, 8 Hz), 7.43 (1H, s), 8.51 (1H, s), 9.67 (1H, d, J=8 Hz), 12.58 (1H, broad s)

EXAMPLE 20

7-[2-(2-Formamidothiazol-4-yl)-2-methoxyiminoacetamido]-3-methylthiomethyl-3-cephem-4-carboxylic acid (syn isomer) (0.64 g) was obtained by reacting tert-butyl 7-[2-(2-formamidothiazol-4-yl)-2-methoxyiminoacetamido]-3-methylthiomethyl-3-cephem-4-carboxylate (syn isomer) (0.9 g) with trifluoroacetic acid (5.8 g) in the pressure of anisole (0.9 ml) according to the similar manner to that of Example 19.

IR (Nujol): 3250, 1780, 1660 cm$^{-1}$

NMR δ ppm (DMSO-d$_6$): 1.99 (3H, s), 3.38–4.1 (4H, m), 3.93 (3H, s), 5.25 (1H, d, J=5 Hz), 5.79 (1H, dd, J=5 Hz, 8 Hz), 7.45 (1H, s), 8.43 (1H, s), 9.69 (1H, d, J=8 Hz), 12.68 (1H, broad s)

The compounds described in the following Examples 21 and 22 were obtained by reacting tert-butyl ester of the corresponding cephalosporanic acid derivatives with trifluoroacetic acid in the presence of anisole according to the similar manner to that of Example 19.

EXAMPLE 21

7-[2-(2-Aminothiazol-4-yl)-2-methoxyiminoacetamido]-3-methoxymethyl-3-cephem-4-carboxylic acid hydrochloride (syn isomer)

IR (Nujol): 3300, 1780, 1720, 1660, 1640 cm$^{-1}$

EXAMPLE 22

7-[2-(2-Aminothiazol-4-yl)-2-methoxyiminoacetamido]-3-methylthiomethyl-3-cephem-4-carboxylic acid (syn isomer)

IR (Nujol): 3350, 1770, 1670 cm$^{-1}$

EXAMPLE 23

To a suspension of 7-[2-(2-formamidothiazol-4-yl)-2-methoxyiminoacetamido]-3-methoxymethyl-3-cephem-3-cephem-4-carboxylic acid (syn isomer) (0.52 g) in a mixture of methanol (3 ml) and tetrahydrofuran (2 ml) was added conc. hydrochloric acid (0.18 g), and the mixture was stirred at 30° C. for 4 hours. After the reaction mixture was cooled and diluted with diisopropyl ether, the precipitated crystals were collected by filtration, washed with diisopropyl ether and then dried to give 7-[2-(2-aminothiazol-4-yl)-2-methoxyiminoacetamido]-3-methoxymethyl-3-cephem-4-carboxylic acid hydrochloride (syn isomer) (0.45 g).

IR (Nujol): 3300, 1780, 1720, 1660, 1640 cm$^{-1}$

NMR δ ppm (DMSO-d$_6$): 3.26 (3H, s), 3.58 (2H, broad s), 4.0 (3H, s), 4.24 (2H, s), 6.24 (1H, d, J=6 Hz), 5.82 (1H, dd, J=5 Hz, 8 Hz), 7.01 (1H, s), 9.87 (1H, d, J=8 Hz)

EXAMPLE 24

7-[2-(2-Aminothiazol-4-yl)-2-methoxyiminoacetamido]-3-methylthiomethyl-3-cephem-4-carboxylic acid (syn isomer) (0.23 g) was obtained by reacting 7-[2-(2-formamidothiazol-4-yl)-2-methoxyiminoacetamido]-3-methylthiomethyl-3-cephem-4-carboxylic acid (syn isomer) (0.6 g) with conc. hydrochloric acid (0.4 g) in a mixture of methanol (3 ml) and tetrahydrofuran (1 ml) according to the similar manner to that of Example 23.

IR (Nujol): 3350, 1770, 1670 cm$^{-1}$

NMR δ ppm (DMSO-d$_6$): 2.01 (3H, s), 3.2–4.1 (4H, m), 3.88 (3H, s), 5.25 (1H, d, J=5 Hz), 5.78 (1H, dd, J=5 Hz, 8 Hz), 6.82 (1H, s), 7.24 (2H, broad s), 9.64 (1H, d, J=8 Hz)

EXAMPLE 25

To a solution of benzhydryl 7-amino-3-methylthiomethyl-3-cephem-4-carboxylate (10 g) and trimethylsilylacetamide (18.4 g) in methylene chloride (100 ml) was added at −15° C. an activated acid, which was prepared from (2-formamidothiazol-4-yl)glyoxylic acid (6.56 g), N,N-dimethylformamide (2.92 ml) and phosphorus oxychloride (3.46 ml) in a conventional manner, and the mixture was stirred at −20° to −15° C. for 15 minutes. After the reaction mixture was poured into water, it was extracted with ethyl acetate. The extract was washed with an aqueous solution of sodium bicarbonate and an aqueous solution of sodium chloride, followed by drying over anhydrous magnesium sulfate. Removal of the solvent gave a residue (13.4 g), which was chromatographed on silica gel (100 ml) using a mixture of benzene and ethyl acetate (5:1 by volume) as an eluent. The fractions containing the desired compound were collected and then evaporated to dryness to obtain benzhydryl 7-[(2-formamidothiazol-4-yl)glyoxylamido]-3-methylthiomethyl-3-cephem-4-carboxylate (7.1 g).

I.R. (Nujol): 3300, 1780, 1700, 1656 cm$^{-1}$

N.M.R. δ ppm (DMSO-d$_6$): 1.83 (3H, s), 3.58 (2H, broad s), 3.67 (2H, broad s), 5.33 (1H, d, J=5 Hz), 5.87 (1H, dd, J=5 Hz, 8 Hz), 6.90 (1H, s), 7.40 (10H, s), 8.47 (1H, s), 8.58 (1H, s), 9.88 (1H, d, J=8 Hz), 12.68 (1H, broad s)

The following compounds were obtained by reacting 7-amino-3-substituted cephalosporanic acid derivatives with the corresponding acids according to the similar manner to that of Example 25.

EXAMPLE 26

7-[(2-Aminothiazol-4-yl)glyoxylamido]-3-methylthiomethyl-3-cephem-4-carboxylic acid.

I.R. (Nujol): 3300, 1762, 1522 cm$^{-1}$

EXAMPLE 27

7-[2-(2-Aminothiazol-4-yl)-DL-glycinamido]-3-methylthiomethyl-3-cephem-4-carboxylic acid.

I.R. (Nujol): 3300, 1755, 1686, 1600 cm$^{-1}$

EXAMPLE 28

To a mixture of benzhydryl 7-amino-3-methylthiomethyl-3-cephem-4-carboxylate (4.92 g) and N-tertbutoxycarbonyl-2-(2-formamidothiazol-4-yl)-DL-glycine (4.0 g) in methylene chloride (100 ml) and tetrahydrofuran (80 ml) was added N,N'-dicyclohexylcarbodiimide (2.39 g), and the mixture was stirred at ambient temperature for an hour. After the insoluble substance was removed by filtration, the filtrate was evaporated to dryness to give a residue, which was dissolved in ethyl acetate. This solution was washed with an aqueous solution of sodium bicarbonate and an aqueous solution of sodium chloride, and then dried over anhydrous magnesium sulfate. Removal of the solvent gave benzhydryl 7-[N-tert-butoxycarbonyl-2-(2-formamidothiazol-4-yl)-DL-glycinamido]-3-methylthiomethyl-3-cephem-4-carboxylate (9.4 g).

I.R. (Nujol): 3300, 1770, 1710, 1680, 1615 cm$^{-1}$

N.M.R. δ ppm (DMSO-d$_6$) 1.36 (9H, s), 1.80 (3H, s), 3.58 (4H, m), 5.16 (d, J=5 Hz) 5.23 (d, J=5 Hz)) (1H) 5.38 (1H, d, J=8 Hz), 5.6–5.9 (1H, m), 6.90 (1H, s), 7.13 (1H, s), 7.33 (10H, broad s), 8.47 (1H, s), 9.08 (1H, d, J=8 Hz)

EXAMPLE 29

A mixture of 7-[(2-formamidothiazol-4-yl)-glyoxylamido] 3-methylthiomethyl-3-cephem-4-carboxylic acid (3.0 g) and conc. hydrochloric acid (3 ml) in methanol (50 ml) was stirred at ambient temperature for 2 hours. The reaction mixture was adjusted to pH 5–6 with an aqueous solution of sodium bicarbonate and then concentrated under reduced pressure. The precipitated crystals in the concentrate were collected by filtration to give 7-[(2-aminothiazol-4-yl)glyoxylamido]-3-methylthiomethyl-3-cephem-4-carboxylic acid (1.1 g).

I.R. (Nujol): 3300, 1762, 1522 cm$^{-1}$

N.M.R. δ ppm (DMSO-d$_6$): 2.00 (3H, s), 3.65 (4H, broad s), 5.22 (1H, d, J=5 Hz), 5.68 (1H, dd, J=5 Hz, 8 Hz), 7.37 (2H, broad s), 7.83 (1H, s), 9.73 (1H, d, J=8 Hz)

EXAMPLE 30

A mixture of benzhydryl 7-[N-tert-butoxycarbonyl-2-(2-formamidothiazol-4-yl)-DL-glycinamido]-3-methylthiomethyl-3-cephem-4-carboxylate (9.4 g) and conc. hydrochloric acid (4.16 ml) in methanol (100 ml) and tetrahydrofuran (25 ml) was stirred at 30° to 55° C. for 5 hours. The reaction mixture was adjusted to pH 4.5 with sodium bicarbonate and then evaporated to dryness to give a residue, which was dissolved in ethyl acetate. This solution was washed with an aqueous solution of sodium chloride, dried over anhydrous magnesium sulfate and then evaporated to obtain benzhydryl 7-[N-tert-butoxycarbonyl-2-(2-aminothiazol-4-yl)-DL-glycinamido]-3-methylthiomethyl-3-cephem-4-carboxylate (7.4 g).

I.R. (Nujol): 3300, 1772, 1716, 1685, 1623, 1244, 1170, 1160 cm$^{-1}$

N.M.R. δ ppm (DMSO-d$_6$): 1.40 (9H, s), 1.80 (3H, s), 3.6 (4H, m), 5.0–5.4 (2H, m), 5.6–5.9 (2H, m), 6.93 (1H, s), 7.30 (1H, s), 7.43 (10H, broad s), 8.93 (1H, d, J=8 Hz)

The following compounds were obtained by reacting 7-acylamino-3-substituted cephalosporanic acid derivatives having a formamido group with hydrochloric acid according to the similar manner to that of Example 30.

EXAMPLE 31

7-[2-(2-Aminothiazol-4-yl)-DL-glycinamido]-3-methylthiomethyl-3-cephem-4-carboxylic acid.

I.R. (Nujol): 3300, 1755, 1686, 1600 cm$^{-1}$

EXAMPLE 32

7-[2-(2-Aminothiazol-4-yl)-DL-glycolamido]-3-methylthiomethyl-3-cephem-4-carboxylic acid.

I.R. (Nujol): 3300, 1752, 1675, 1600 cm$^{-1}$

EXAMPLE 33

Benzhydryl 7-[(2-formamidothiazol-4-yl)glyoxylamido]-3-methylthiomethyl-3-cephem-4-carboxylate (7.0 g) was dissolved in a solution of methylene chloride (70 ml), anisole (7 ml) and trifluoroacetic acid (14 ml), and the mixture was stirred at ambient temperature for an hour. After the solvent was removed by distillation under reduced pressure, the residue was dissolved in water, adjusted to pH 2.0 with conc. hydrochloric acid and then extracted with ethyl acetate. The extract was washed with an aqueous sodium chloride and dried over magnesium sulfate, followed by evaporation. The residue was pulverized with diisopropyl ether to obtain 7-[(2-formamidothiazol-4-yl)glyoxylamido]-3-methylthiomethyl-3-cephem-4-carboxylic acid (3.3 g).

I.R. (Nujol): 3120, 1762, 1731, 1677 cm$^{-1}$

N.M.R. δ ppm (DMSO-d$_6$): 2.00 (3H, s), 3.63 (4H, broad s), 5.24 (1H, d, J=5 Hz), 5.73 (1H, dd, J=5 Hz, 8 Hz), 8.43 (1H, s), 8.57 (1H, s), 9.90 (1H, d, J=8 Hz), 12.80 (1H, broad s)

The following compounds were obtained by reacting 7-acylamino-3-substituted cephalosporanic acid derivatives having benzhydryl ester with 2,2,2-trifluoroacetic acid in the presence of anisole according to the similar manner to that of Example 33.

EXAMPLE 34

7-[(2-Aminothiazol-4-yl)glyoxylamido]-3-methylthiomethyl-3-cephem-4-carboxylic acid.

I.R. (Nujol) : 3300, 1762, 1522 cm$^{-1}$

EXAMPLE 35

7-[2-(2-Aminothiazol-4-yl)-DL-glycolamido]-3-methylthiomethyl-3-cephem-4-carboxylic acid.

I.R. (nujol) : 3300, 1752, 1675, 1600 cm$^{-1}$

EXAMPLE 36

A mixture of benzhydryl 7-[N-tert-butoxycarbonyl-2-(2-aminothiazol-4-yl)-DL-glycinamido]-3-methylthiomethyl-3-cephem-4-carboxylate (7.0 g), anisole (7 ml) and 2,2,2-trifluoroacetic acid (21 ml) was stirred at 5° C. for half an hour. To the reaction mixture was added dropwise diisopropyl ether (300 ml), and the precipitated substance was collected by filtration and then washed with diisopropyl ether, followed by dissolving in a mixture of ethyl acetate (50 ml) and water (100 ml). After the aqueous layer was separated out, the ethyl acetate in the aqueous layer was completely removed, and then the remained aqueous solution was adjusted to pH 4.2 with 5% aqueous solution of sodium bicarbonate. The resultant aqueous solution was chromatographed on nonionic adsorption resin "Diaion HP.-20" (Trade Mark, made by Mitsubishi Chemical Industries Ltd.) (100 ml). After washing with water (250 ml), elution was carried out with 30% aqueous isopropyl alcohol. The fractions containing the desired compound were collected and then evaporated, followed by lyophilization to obtain 7-[2-(2-aminothiazol-4-yl)-DL-glycinamido]-3-methylthiomethyl-3-cephem-4-carboxylic acid (2.9 g).

I.R. (Nujol) : 3300, 1755, 1686, 1600 cm$^{-1}$

N.M.R. δppm (D$_2$O+DC1) : 2.07 (3H, s), 3.5–4.0 (4H, m), 5.27 (1H, d, J=5 Hz), 5.50 (1H, s), 5.60 (d, J=5 Hz) 5.72 (d, J=5 Hz)) (1H), 7.27 (1H, s)

EXAMPLE 37

To a solution of 7-[(2-aminothiazol-4-yl)glyoxylamido]-3-methylthiomethyl-3-cephem-4-carboxylic acid (1.1 g) in methanol (80 ml) was added sodium borohydride (150 mg) at 5° to 10° C., and the mixture was stirred at the same temperature for half an hour. After the reaction mixture was adjusted to pH 5.0 with 10% hydrochloric acid, the solvent was removed by distillation. To the residue was added water (50 ml), followed by adjusting to pH 5.0 with 10% hydrochloric acid. The resultant aqueous solution was chromatographed on nonionic adsorption resin "Diaion HP-20" (50 ml). After washing with water (100 ml), elution was carried out with 30% aqueous isopropyl alcohol. The fractions containing the desired compound were collected and then evaporated to dryness, followed by lyophilization to obtain 7-[2-(2-aminothiazol-4-yl)-DL-glycolamido]-3-methylthiomethyl-3-cephem-4-carboxylic acid (0.75 g).

I.R. (Nujol) : 3300, 1752, 1675, 1600 cm$^{-1}$

N.M.R. δppm (DMSO-d$_6$) : 2.00 (3H, s), 3.48 (2H, broad s), 3.67 (2H, broad s), 4.93 (1H, s), 5.07 (1H, d, J=5 Hz), 5.57 (1H, m), 6.50 (1H, s), 7.03 (2H, broad s), 8.33 (d, J=8 Hz) 8.42 (d, J=8 Hz)) (1H)

EXAMPLE 38

Vilsmeier reagent prepared from phosphorus oxychloride (1.23 ml) and N,N-dimethylformamide (1.1 ml) was suspended in dry tetrahydrofuran (40 ml). To the suspension was added 2-(2-formamidothiazol-4-yl)-2-tert-butoxycarbonylmethoxyiminoacetic acid (syn isomer) (4.0 g) under ice-cooling with stirring, and the mixture was stirred at the same temperature for 50 minutes to prepare the activated acid solution. On the other hand, benzhydryl 7-amino-3-methylthiomethyl-3-cephem-4-carboxylate (4.66 g) and trimethylsilylacetamide (8.6 g) were dissolved in methylene chloride (50 ml). To the solution was added the activated acid solution at −20° C. at a time, and the mixture was stirred at the same temperature for an hour. Water (100 ml) and ethyl acetate (200 ml) were added to the resultant solution, and the organic layer was separated, washed with 5% aqueous sodium bicarbonate and an aqueous sodium chloride, and then dried over magnesium sulfate, followed by evaporation under reduced pressure to give benzhydryl 7-[2-(2-formamidothiazol-4-yl)-2-tert-butoxycarbonylmethoxyiminoacetamido]-3-methylthiomethyl-3-cephem-4-carboxylate (syn isomer) (8.0 g), mp 132°–138° C.

IR (Nujol) : 3260, 1783, 1725, 1687 cm$^{-1}$

NMR δppm (DMSO-d6, δ): 1.47 (9H, s), 1.83 (3H, s), 3.60 (2H, broad s), 3.66 (2H, broad s), 4.98 (2H, broad s), 5.32 (1H, d, J=5 Hz), 5.92 (1H, dd, J=5 Hz, 8 Hz), 6.95 (1H, s), 7.4 (10H, m), 7.48 (1H, s), 8.54 (1H, s), 9.63 (1H, d, J=8 Hz), 12.65 (1H, broad s)

EXAMPLE 39

Benzhydryl 7-[2-(2-formamidothiazol-4-yl)-2-benzhydryloxycarbonylmethoxyiminoacetamido]-3-methylthiomethyl-3-cephem-4-carboxylate (syn isomer) (7.8 g) was obtained by reacting benzhydryl 7-amino-3-methylthiomethyl-3-cephem-4-carboxylate (4.0 g) with the activated acid solution prepared from 2-(2-formamidothiazol-4yl)-2-benzhydryloxycarbonylmethoxyiminoacetic acid (syn isomer) (6.18 g), phosphorus oxychloride (1.42 ml) and N,N-dimethylformamide (1.21 ml), according to a similar manner to that of Example 38, mp 135°–142° C.

IR (Nujol) : 3250, 1780, 1722, 1685 cm$^{-1}$

NMR δppm (DMSO-d6) : 1.83 (3H, s), 3.63 (4H, m), 5.0 (2H, broad s), 5.35 (1H, d, J=5 Hz), 5.98 (1H, dd, J=5 Hz, 8 Hz), 6.95 (1H, s), 6.98 (1H, s), 7.37 (20H, m), 7.50 (1H, s), 8.57 (1H, s), 9.82 (1H, d, J=8 Hz), 12.73 (1H, broad s)

EXAMPLE 40

Benzhydryl 7-[2-benzhydryloxycarbonylmethoximino-2-{2-(2,2,2-trifluoroacetamido)thiazol-4-yl}acetamido]-3-methylthiomethyl-3-cephem-4-carboxylate (syn isomer) (5.6 g) was obtained by reacting benzhydryl 7-amino-3-methythiomethyl-3-cephem-4-carboxylate (3.0 g) with the activated acid solution prepared from 2-benzhydryloxycarbonylmethoximino-2-[2-(2,2,2-trifluoroacetamido)thiazol-4-yl]acetic acid (syn isomer) (3.68 g), phosphorus oxychloride (0.89 ml) and N,N-dimethylformamide (0.75 ml), according to a similar manner to that of Example 38, mp 165°–169° C.

IR (Nujol) : 3300, 1786, 1733, 1675, 1610 cm$^{-1}$

NMR δppm (DMSO-D6) : 2.00 (3H, s), 3.56 (4H, m), 4.84 (2H, s), 5.26 (1H, d, J=5 Hz), 5.86 (1H, dd J=5 Hz, 8 Hz), 6.84 (1H, s), 6.88 (1H, s), 7.3 (20H, m), 9.62 (1H, d, J=8 Hz)

EXAMPLE 41

To a suspension of benzhydryl 7-[2-( 2-formamidothiazol-4-yl)-2-tert-butoxycarbonylmethoxyiminoacetamido]-3-methylthiomethyl-3-cephem-4-carboxylate (syn isomer) (8.0 g) in methanol (160 ml) wad added conc. hydrochloric acid (5.6 ml), and the mixture was stirred at 35° C. for an hour. The resultant solution was adjusted to pH 5.0 with a saturated aqueous sodium bicarbonate. After distilling methanol under reduced pressure, the residue was dissolved in water (100 ml) and ethyl acetate (200 ml). The ethyl acetate layer was washed with a saturated aqueous sodium chloride and dried over magnesium sulfate. The solvent was removed by filtration to give benzhydryl 7-[2-(2-aminothiazol-4-yl)-2-tert-butoxycarbonylmethoxyiminoacetamido]-3-methylthiomethyl-3-cephem-4-carboxylate (syn isomer) (7.0 g), mp 140°–145° C.

IR (Nujol) : 3250, 1780, 1723, 1680 cm$^{-1}$

NMR δppm (DMSO-d6) : 1.43 (9H, s), 1.83 (3H, s), 3.63 (4H, m), 4.6 (2H, broad s), 5.29 (1H, d, J=5 Hz), 5.87 (1H, dd, J=5 Hz, 8 Hz), 6.83 (1H, s), 6.95 (1H, s), 7.4 (10H, m), 9.52 (1H, d, J=8 Hz)

EXAMPLE 42

Benzhydryl 7-[2-(2-aminothiazol-4-yl)-2-benzhydryloxycarbonylmethoxyiminoacetamido]-3-methylthiomethyl-3-cephem-4-carboxylate (syn isomer) (7.0 g), mp 148°–155° C., was obtained by reacting benzhydryl 7-[2-(2-formamidothiazol-4-yl)-2-benzhydryloxycarbonylmethoxyiminoacetamido]-3-methylthiomethyl-3-cephem-4-carboxylate (syn isomer) (7.5 g) with conc. hydrochloric acid (3.9 ml) according to a similar manner to that of Example 41.

NMR δ ppm (DMSO-d6): 1.83 (3H, s), 3.60 (4H, m), 4.90 (2H, broad s), 5.30 (1H, d, J=5 Hz), 5.87 (1H, dd, J=5 Hz, 8 Hz), 6.86 (1H, s), 6.93 (1H, s), 6.97 (1H, s), 7.4 (20H, m), 9.67 (1H, d, J=8 Hz).

EXAMPLE 43

A solution of 7-[2-carboxymethoxyimino-2-{2-(2,2,2-trifluoroacetamido)thiazol-4-yl}acetamido]-3-methylthiomethyl-3-cephem-4-carboxylic acid (syn isomer) (4.1 g) and sodium acetate (9.56 g) in water (41 ml) was stirred for 19.5 hours at ambient temperature. The resultant solution was adjusted to pH 2.0 with conc. hydrochloric acid. The precipitates were collected by filtration and dried over phosphorus pentoxide to give 7-[2-carboxymethoxyimino-2-(2-aminothiazol-4-yl)acetamido]-3-methylthiomethyl-3-cephem-4-carboxylic acid (syn isomer) (1.8 g), mp 173°–176° C. (dec.).

IR (Nujol): 3370, 1772, 1670 (broad) cm$^{-1}$

NMR δ ppm (DMSO-d6): 2.00 (3H, s), 3.57 (4H, m), 4.60 (2H, broad s), 5.17 (1H, d, J=5 Hz), 5.73 (1H, dd, J=5 Hz, 8 Hz), 6.77 (1H, s), 9.45 (1H, d, J=8 Hz)

EXAMPLE 44

To a solution of benzhydryl 7-[2-benzhydryloxycarbonylmethoxyimino-2-{2-(2,2,2-trifluoroacetamido)thiazol-4-yl}acetamido]-3-methylthiomethyl-3-cephem-4-carboxylate (syn isomer) (5.6 g) and anisole (5.6 ml) in methylene chloride (11.2 ml) was added trifluoroacetic acid (11.2 ml) at 10° C. The mixture was stirred for 1.5 hours at ambient temperature and then poured into a mixture of diisopropyl ether (400 ml) and petroleum ether (100 ml). The precipitates were collected by filtration and washed with petroleum ether to give 7-[2-carboxymethoxyimino-2-{2-(2,2,2-trifluoroacetamido)thiazol-4-yl}acetamido]-3-methylthiomethyl-3-cephem-4-carboxylic acid (syn isomer) (4.2 g), mp 183°–186° C. (dec.).

IR (Nujol): 3300, 1778, 1723, 1660 cm$^{-1}$

NMR δ ppm (DMSO-d6): 2.00 (3H, s), 3.62 (4H, m), 4.70 (2H, s), 5.24 (1H, d, J=5 Hz), 5.80 (1H, dd, J=5 Hz, 8 Hz), 7.60 (1H, s), 9.68 (1H, d, J=8 Hz)

What we claim is:

1. A compound of the formula:

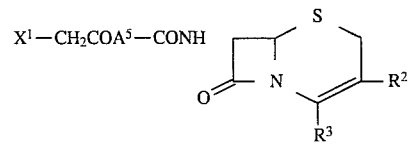

in which

R$^2$ is lower alkoxymethyl, lower alkylthiomethyl or lower alkenylthiomethyl,

R$^3$ is carboxy or a protected carboxy group,

A$^5$ is lower alkylene which may have a group of the formula: =N–OR$^6$, wherein R$^6$ is hydrogen, lower alkenyl, lower alkynyl, lower alkyl or lower alkyl substituted by one or more substituent(s) selected from carboxy, a protected carboxy group, amino a protected amino group and a heterocyclic group, and X$^1$ is halogen, or a salt thereof.

2. A compound of claim 1, in which

R$^2$ is lower alkoxymethyl or lower alkylthiomethyl, and

A$^5$ is methylene or a group of the formula:

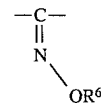

wherein R$^6$ is hydrogen, lower alkenyl, lower alkynl, lower alkyl or lower alkyl substituted by carboxy or a protected carboxy group.

3. A compound of claim 1, which

R$^2$ is lower alkoxymethyl,

R$^3$ is carboxy or esterified carboxy, and

A$^5$ is a group of the formula:

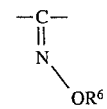

wherein R$^6$ is hydrogen or lower alkyl.

4. A compound of claim 2, in which

R$^2$ is methoxymethyl and

R$^6$ is lower alkyl.

5. A compound of claim 2, in which

R$^2$ is methoxymethyl and

R$^6$ is hydrogen.

* * * * *